United States Patent
Hassibi et al.

(10) Patent No.: US 10,739,293 B2
(45) Date of Patent: Aug. 11, 2020

(54) ACTIVE-ELECTRODE INTEGRATED BIOSENSOR ARRAY AND METHODS FOR USE THEREOF

(71) Applicant: Board of Regents, The University of Texas System, Austin, TX (US)

(72) Inventors: Arjang Hassibi, Austin, TX (US); Arun Manickam, Sunnyvale, CA (US); Rituraj Singh, Sunnyvale, CA (US)

(73) Assignee: Board of Regents, The University of Texas Systems, Austin, TX (US)

(*) Notice: Subject to any disclaimer, the term of this patent is extended or adjusted under 35 U.S.C. 154(b) by 241 days.

(21) Appl. No.: 15/097,037

(22) Filed: Apr. 12, 2016

(65) Prior Publication Data

US 2016/0231270 A1 Aug. 11, 2016

Related U.S. Application Data

(63) Continuation of application No. 13/527,742, filed on Jun. 20, 2012, now Pat. No. 9,341,589.

(51) Int. Cl.
| | | |
|---|---|---|
| *C12P 19/34* | (2006.01) | |
| *G01N 27/27* | (2006.01) | |
| *C12Q 1/6874* | (2018.01) | |
| *G01N 27/327* | (2006.01) | |

(52) U.S. Cl.
CPC ........... *G01N 27/27* (2013.01); *C12Q 1/6874* (2013.01); *G01N 27/3276* (2013.01)

(58) Field of Classification Search
USPC ......... 435/6.1, 6.11, 6.12, 91.1, 91.2, 91.51; 436/94, 501; 536/23.1, 24.3, 24.33, 25.3
See application file for complete search history.

(56) References Cited

U.S. PATENT DOCUMENTS

| | | |
|---|---|---|
| 5,323,115 A | 6/1994 | Werner, Jr. |
| 6,469,524 B1 | 10/2002 | Oberdier |
| 6,472,887 B1 | 10/2002 | Tullis et al. |
| 6,724,324 B1 | 4/2004 | Lambert |
| 7,504,832 B2 | 3/2009 | Kandori et al. |
| 7,835,871 B2 | 11/2010 | Kain et al. |
| 7,948,015 B2 | 5/2011 | Rothberg et al. |

OTHER PUBLICATIONS

"Insulator (electricity)" from Wikipedia, the free encyclopedia. Printed on Dec. 13, 2018.*
Diehl et al., "BEAMing: Single-Molecule PCR on Microparticles in Water-in-Oil Emulsions," Nature Methods, vol. 3, No. 7, pp. 551-559, Jun. 21, 2006.
Margulies et al., "Genome Sequencing in Microfabricated High-Density Picolitre Reactors," Nature, vol. 437, pp. 376-380, Sep. 15, 2005.
Merrifield, R. B., "Solid-Phase Peptide Synthesis. III. An Improved Synthesis of Bradykinin," Biochemistry, vol. 3, No. 9, pp. 1385-1390, Sep. 1964.
Pourmand et al., "Direct Electrical Detection of DNA Synthesis," PNAS, vol. 103, No. 17, pp. 6466-6470, Apr. 25, 2006.
Rothberg et al., "An Integrated Semiconductor Device Enabling Non-Optical Genome Sequencing," Nature, vol. 475, pp. 348-352, Jul. 21, 2011.
Rothberg et al., "The Development and Impact of 454 Sequencing," Nature Biotechnology, vol. 26, No. 10, pp. 1117-1124, Oct. 9, 2008.
Sakurai et al., "Real-Time Monitoring of Dna Polymerase Reactions by a Micro ISFET pH Sensor," Anal. Chem., vol. 64, No. 17, pp. 1996-1997, Sep. 1, 1992.
Michael L. Metzker, "Sequencing Technologies for the Next Generation," Nature Reviews Genetics, pp. 31-46, Jan. 2010.
Rothe et al., "Multi-Target Electrochemical Biosensing Enabled by Integrated CMOS Electronics," Journal of Micromechanics and Microengineering, vol. 21, pp. 1-10, 2011.

* cited by examiner

*Primary Examiner* — Frank W Lu
(74) *Attorney, Agent, or Firm* — Robert A. Voigt, Jr.; Winstead PC

(57) ABSTRACT

A method and device for performing DNA sequencing and extracting structural information from unknown nucleic acid strands. The device includes a microwell structure, where identical DNA strands are immobilized within the microwell structure on a surface of a micro-bead, an active electrode or a porous polymer. The device further includes a CMOS-integrated semiconductor integrated circuit, where the CMOS-integrated semiconductor integrated circuit includes metal layers on a silicon substrate, where the metal layers form an active electrode biosensor. In addition, a sensing electrode is formed by creating openings in a passivation layer of the CMOS-integrated semiconductor integrated circuit to hold a single bead, on which the DNA strands are immobilized.

15 Claims, 17 Drawing Sheets

Specification includes a Sequence Listing.

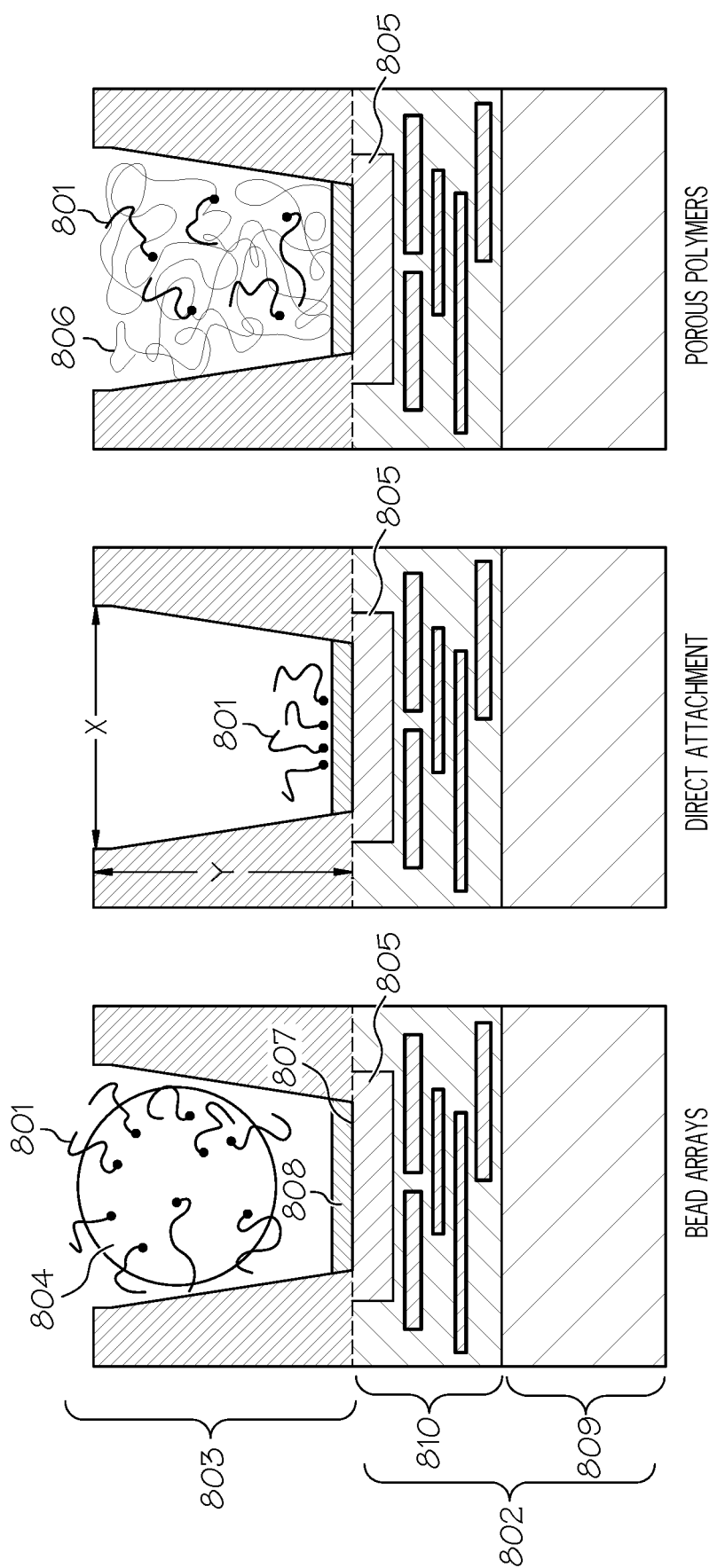

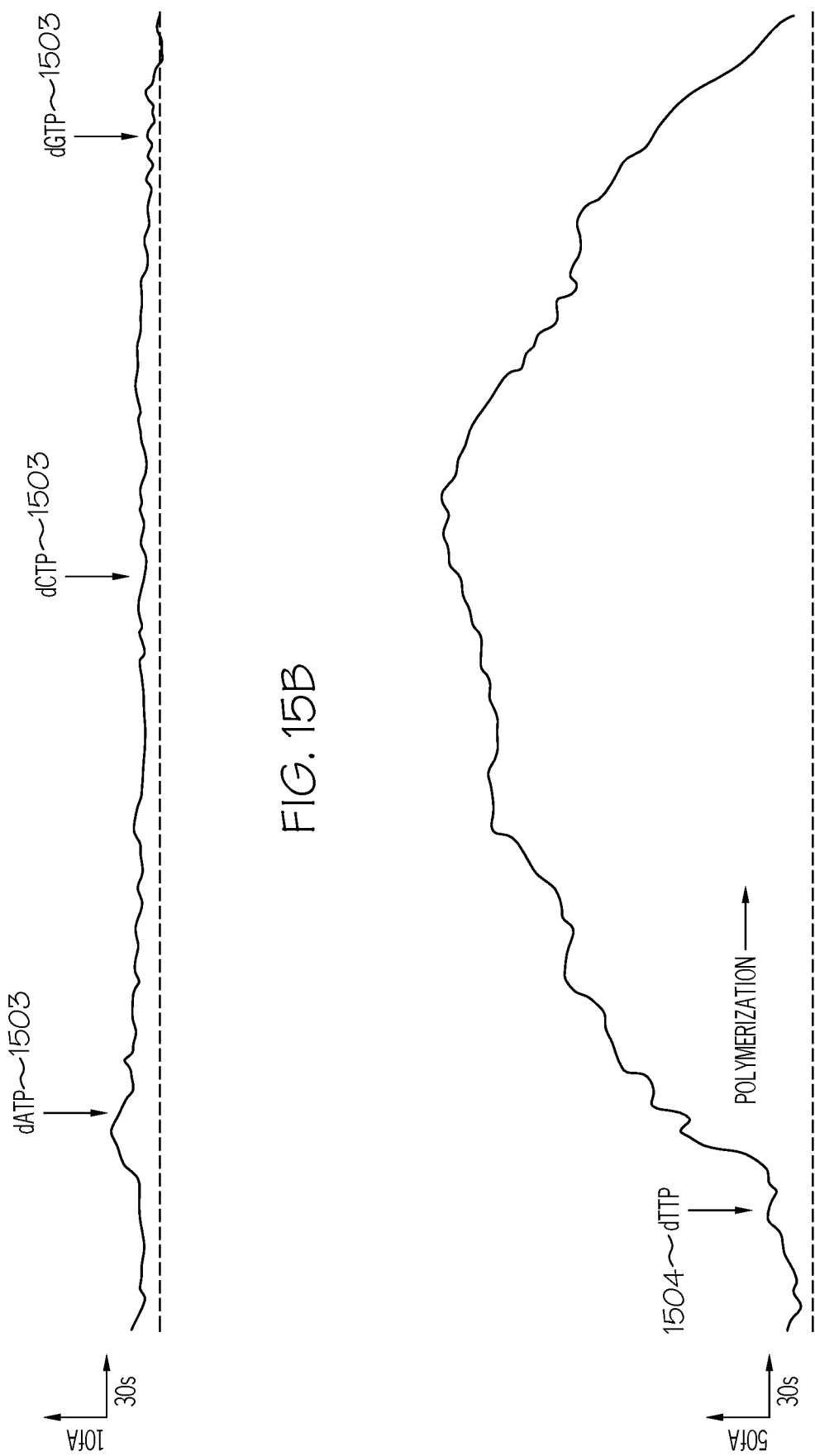

ACTIVE-ELECTRODE INTEGRATED BIOSENSOR ARRAY AND METHODS FOR USE THEREOF

TECHNICAL FIELD

The present invention relates generally to biosensors and bioelectronics, and more particularly to a type of electro-analytical biosensor, referred to herein as the "active-electrode" biosensor, that is compatible with Very Large Scale Integration (VLSI) manufacturing processes and is used in genomics and proteomics applications.

BACKGROUND

Biosensors are devices that use biochemical reactions to identify and detect various molecules and biochemical analytes. Biosensors are widely used in different life-science applications, ranging from environmental monitoring and basic life science research to Point-of-Care (PoC) in-vitro molecular diagnostics. Biosensors are known to be very sensitive and also extremely versatile in terms of detection as they can detect a small number of almost any kind of analyte, once a proper recognition molecule is identified. Example analytes that have been detected using biosensors include DNA and RNA strands, proteins, metabolites, toxins, micro-organisms, and even explosives molecules.

All biosensors, independent of the analyte they are trying to detect, include two key building blocks. One is the molecular recognition layer which is responsible for identifying and/or interacting with and/or reacting with and/or capturing the specific target analyte from the sample. The other is the sensor apparatus that detects and/or quantifies the interactions of the recognition layer with the analyte and provides a measurable output signal, generally in the form of an electrical signal. The molecular recognition layer typically comprises of carefully engineered and surface-assembled bio-molecules in the form of spotted or synthesized DNA oligonucleotides, aptamers, and antibodies attached to solid substrates, such as glass slides, micro-beads, electrodes, semiconductor materials, or dense polymers while the sensor includes optical-, MEMS- and/or electronics-based transducers connected to a low-noise detection circuit.

So far, there have been many detection methods that have been adopted in biosensor systems. A detection method is defined as the specific type of physiochemical mechanism designed into the molecular recognition layer, analytes, and the interaction environments that make the identification of the specific target analytes possible by the sensor. The most widely used detection methods are different classes of optical (e.g., fluorescence, bioluminescence) and electro-analytical (e.g., potentiometric, amperometric, impedimetric). It is also common to classify biosensors based on their detection method. For example, in bioluminescence-based biosensors, the interaction of the analyte and probes results in a bioluminescence phenomenon which is detected by a specific sensor with a transducer sensitive to bioluminescence signals.

Electro-analytical biosensors detect analytes by monitoring different electronic changes in electrode-electrolyte transducers that are specifically interfaced with a recognition layer. For instance, in amperometric biosensors, low-frequency Faradaic reduction-oxidation (redox) currents are used as an indicator for analyte interactions with the recognition layer, whereas in impedimetric biosensors, the changes in the electrode-electrolyte impedance induced by the captured analyte are used as an indicator of analyte interactions with the recognition layer.

Unfortunately, the existing state-of-the-art electro-analytical biosensors are not compatible with semiconductor Very Large Scale Integration (VLSI) manufacturing processes thereby not being able to take advantage of the VLSI processes (e.g., highest level of integration, miniaturization, cost-efficiency, and robustness).

SUMMARY

As discussed above, the existing state-of-the-art electro-analytical biosensors are not compatible with semiconductor Very Large Scale Integration (VLSI) manufacturing processes thereby not being able to take advantage of the VLSI processes (e.g., highest level of integration, miniaturization, cost-efficiency, and robustness). The principles of the present invention address this impediment.

In view of the limitations of biosensors currently available, there is a need for improved biosensors and methods for use thereof in fields, such as nucleic acid detection, nucleic acid sequencing, proteomics, forensics, in-vitro diagnostics, medicine, and the like. Needed improvements include reducing the cost, increasing the throughput, and/or decreasing the size of biosensors instrument; in order to advance the field of personalized medicine for example.

Provided herein are Complementary Metal Oxide Semiconductor (CMOS) biological sensors ("biosensors") fabricated using Very Large Scale Integration (VLSI) manufacturing processes in various applications, such as, for example, nucleic acid sequencing, proteomics, and forensics. CMOS biosensors described in various embodiments of the present invention can be used in a variety of genomics and proteomics applications. In particular, they can be used in nucleic acid sequencing, such as deoxyribonucleic acid (DNA) sequencing, ribonucleic acid (RNA) sequencing, and forensics analysis, such as short tandem repeat (STR) analysis.

In one embodiment of the present invention, a method for assaying for a presence of a nucleic acid sequence in a nucleic acid sample comprises providing a chip comprising (i) a plurality of wells, where an individual well of the plurality of wells comprises a porous polymer, a template nucleic acid molecule derived from the nucleic acid sample and reagents necessary for a polymerization reaction, and (ii) a sensor adjacent to the individual well, where the sensor detects signals indicative of the presence of the nucleic acid sequence in the template nucleic acid molecule. The method further comprises subjecting the template nucleic acid molecule to the polymerization reaction under conditions that are sufficient to yield a nucleic acid strand that is complementary to the template nucleic acid molecule. The method additionally comprises using the sensor to detect the signals indicative of the presence of the nucleic acid sequence in the template nucleic acid molecule. Furthermore, the method comprises based on the signals detected in (c), providing an output that is indicative of the presence of the nucleic acid sequence in the nucleic acid sample.

In another embodiment of the present invention, a system for assaying for a presence of a nucleic acid sequence in a nucleic acid sample comprises a chip comprising (i) a plurality of wells, where during use, an individual well of the plurality of wells comprises a porous polymer, a template nucleic acid molecule derived from the nucleic acid sample and reagents necessary for a polymerization reaction, and (ii) a sensor adjacent to the individual well, where the sensor detects signals indicative of the presence of the nucleic acid sequence in the template nucleic acid molecule. The system further comprises detection circuitry operatively coupled to the sensor, where the detection circuitry (i) detects the signals indicative of the presence of the nucleic acid sequence in the template nucleic acid molecule when the template nucleic acid molecule is subjected to the polymerization reaction under conditions that are sufficient to yield a nucleic acid strand that is complementary to the template nucleic acid molecule, and (ii) provides an output that is indicative of the presence of the nucleic acid sequence in the nucleic acid sample.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The novel features of the present invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 8A-8C illustrate different embodiments for immobilizing identical DNA in proximity of an active electrode in accordance with an embodiment of the present invention;

FIGS. 14A-14C illustrate interface capacitance measurements versus solution pH in accordance with an embodiment of the present invention;

FIGS. 15A-15C illustrate DNA polymerization detection in accordance with an embodiment of the present invention.

DETAILED DESCRIPTION

Incorporation by Reference

Figure 1:
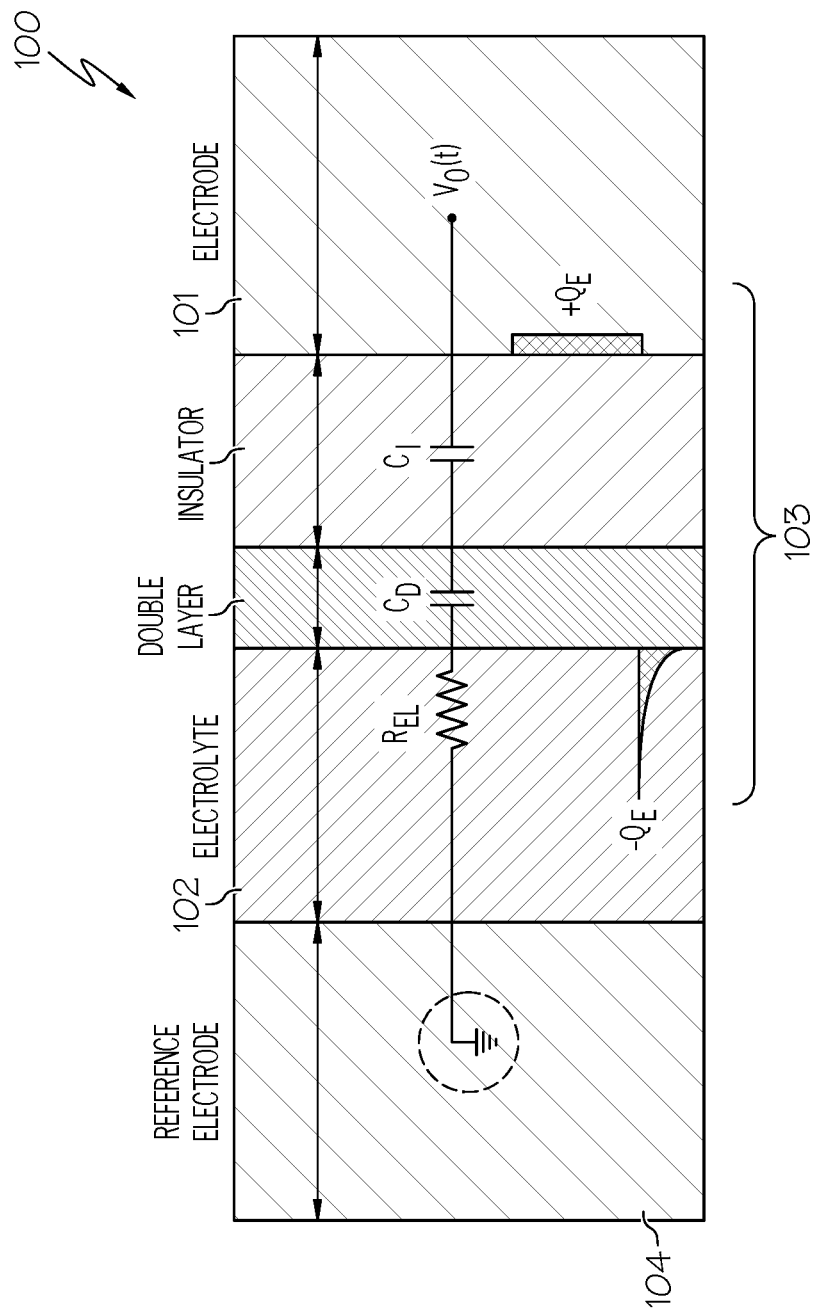
FIG. 1 illustrates an active electrode circuit model in accordance with an embodiment of the present invention.

All publications, patents, and patent applications mentioned in this specification are herein incorporated by reference to the same extent as if each individual publication, patent, or patent application was specifically and individually indicated to be incorporated by reference.

Principles of the Present Invention

While various embodiments of the present invention have been shown and described herein, it will be obvious to those skilled in the art that such embodiments are provided by way of example only. Numerous variations, changes, and substitutions may occur to those skilled in the art without departing from the present invention. It should be understood that various alternatives to the embodiments of the present invention described herein may be employed in practicing the invention.

The principles of the preset invention relate to electro-analytical biosensors. Generally speaking, electro-analytical biosensors that detect analytes by monitoring different electronic changes in electrode-electrolyte transducers that are specifically interfaced with the recognition layers. For instance, in amperometric biosensors, low-frequency Faradaic reduction-oxidation currents are used as an indicator for analyte interactions with the recognition layer, whereas in impedimetric biosensors, the changes in the electrode-electrolyte impedance induced by the captured analyte are used as an indicator of analyte interactions with the recognition layer.

It is noted that depending on the exact electrical characteristic that is being probed (or monitored) in electro-analytical biosensors, different instrumentation techniques and electrode configurations are required. The principles of the present invention described herein describe a specific type of electro-analytical biosensor, called an active-electrode biosensor, and the methods by which one can create high-performance and highly-parallel DNA sequencing platforms employing this biosensor.

One of the key advantages of active-electrode biosensors is that they are compatible with semiconductor Very Large Scale Integration (VLSI) manufacturing processes in general, and Complementary Metal-Oxide-Semiconductor (CMOS) Integrated Circuits (ICs) in particular. This means that all of the advantages of VLSI processes (e.g., highest level of integration, miniaturization, cost-efficiency, and robustness) can be applied to active-electrode biosensors. Furthermore, the principles of the present invention provide methods by which one can design arrays of active-electrode biosensors using CMOS processes. While it is self-evident that the present invention can be used for a variety of biosensing applications, embodiments of the present invention described herein are related to DNA sequencing applications.

There are many different techniques to perform DNA sequencing and extract structural information from unknown nucleic acid strands. Certain embodiments of the present invention may rely on the Sequence-by-Synthesis (SBS) procedure. In SBS, individual nucleotides (dATP, dCTP, dGTP and dTTP) are iteratively introduced to a primed DNA complex in the presence of the DNA polymerase enzyme while the occurrence of polymerization events is monitored. Successful polymerization events at the 3'-terminus of the primer suggest the presence of the complementary base on the template DNA while the amplitude of the polymerization indicates the number of consecutive identical bases. Different techniques have been discussed in the art to detect the polymerization events to perform the SBS procedure. Examples are bioluminescence-based enzymatic cascade, fluorescent-label nucleotides, and pH-based. Embodiments of the present invention described herein provide an alternative electro-analytical technique which is based on using active-electrode biosensors. The key advantages over the previous methods are amenability to VLSI integration, miniaturization capabilities, lower noise performance, and increased detection dynamic range.

Definitions

An active electrode is defined as a highly conductive material (i.e., an electrode) with its electrical potential, $\Phi_0(t)$, set to $V_0(t)$, a defined voltage set by an independent time-varying source, such that $\Phi_0(t)=V_0(t)$ at all time. In the context of electro-analysis and the present invention, an active-electrode system is defined as a conductive material (i.e., the electrode) that is capacitively-coupled to an aqueous and electrically-conductive solution (i.e., the electrolyte) such that the capacitively-coupled electrode-to-electrolyte potential difference, $\Phi_E(t)$, follows $V_0(t)$, such that $\Phi_E(t)=V_0(t)$ at all time.

An active electrode biosensor is defined here as an active electrode system with an electrolyte containing the target analyte in which by applying time-varying $V_0(t)$ and concurrently monitoring the corresponding coupled charge (screening charge) on the highly-conductive electrode, denoted by $Q_E(t)$, one may infer information regarding the target analyte presence, and/or abundance and/or molecular structure.

There are unique characteristics for the active electrodes biosensor described herein. The first is that "capacitively-coupled" means that the active-electrode is not directly in contact with the electrolyte and that an electrically insulating layer with a thickness between 5 nm to 100 nm is placed between the electrode and the electrolyte. The second is that $Q_E(t)$ is located in a very thin layer near the electrode-insulator interface; however, $-Q_E(t)$, the opposite screening charge on the electrolyte-insulator interface side, is distributed non-uniformly within the electrolyte in a form generally referred to in the art as the double layer (i.e., Helmotz and diffusion layers). The third and final characteristic is that $V_0(t)$ can change $Q_E(t)$ as well as the profile of the charge within the double layer. It is known in the art that such changes depend on the exact electrochemical characteristics of the electrolyte (e.g., ionic species charges and their diffusion coefficient), the electrolyte-insulator interface (e.g., surface pKa and the concentration the surface traps for the ions in the electrolyte), and the thickness as well as the material composition of the insulator. In view of the foregoing, no net charge transfer from the electrode to the electrolyte can occur (i.e., no DC current can pass the interface); however, the ionic charges can still electrostatically interact with the charge carriers within the electrode.

Active-Electrode Sensor Circuit Architecture

A simple and widely accepted circuit model 100 for active-electrode sensors is shown in FIG. 1 in accordance with an embodiment of the present invention. Referring to FIG. 1, $C_1$ and $C_D$ represent the insulator layer 101 and double layer 102, respectively, while $R_{EL}$ represents the ohmic resistance of the electrolyte from the electrode-insulator interface 103 to a counter electrode 104 (e.g., Ag/AgCl electrode) in the electrolyte. For typical insulating materials, such as $SiO_2$, $Si_3N_4$, $TiO_2$, $Al_2O_3$ or $HfO_2$, one can safely assume that $C_1$ is a linear capacitor; however, $C_D$ is widely known in the art to be inherently non-linear and function of the voltage placed across it.

Figure 2:
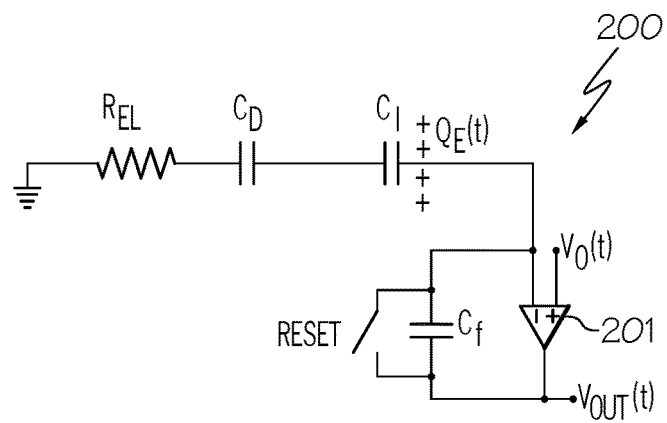
FIG. 2 illustrates an active electrode system using a switch capacitor amplifier sensor in accordance with an embodiment of the present invention.

The fundamental sensor circuitry 200 in the present invention for measuring $Q_E(t)$ is shown in FIG. 2 in accordance with an embodiment of the present invention which is essentially a Switched-Capacitor Charge Amplifier (SCCA). In this circuit, to ensure $\Phi_E(t)=V_0(t)$ at all times, one can take advantage of an operational amplifier 201 with a capacitive negative feedback that connects the (−) input of amplifier 201 to its output, $V_{OUT}(t)$, while $V_0(t)$ is applied to its (+) input. To detect $Q_E(t)$, the following steps occur:

(a) Reset step: First the feedback reset switch is activated (connected) to discharge any accumulated charge on $C_f$ at t=0 such that $V_{OUT}(t)=V_0(t)$.

(b) Read step: Subsequently, at t=Δ, the switch is deactivated (disconnected) and $V_{OUT}(t)$ is read in real time for t>Δ. It can be shown that during this phase $$V_{OUT}(t) = \frac{1}{C_f}[Q_E(t) - Q_E(\Delta)] \quad \text{(EQ 1)}$$

which means that $V_{OUT}(t)$ is effectively the amplified version of the difference between the charge at time t compared with the charge at t=Δ. In most cases, the reset step duration (Δ) can be kept relatively small such that $Q_E(\Delta) \approx Q_E(0)$, thereby resulting in $$V_{OUT}(t) \approx \frac{1}{C_f}[Q_E(t) - Q_E(0)] \quad \text{(EQ 2)}$$

which indicate that $V_{OUT}(t)$ is the amplified version difference between the charge at time t compared with the charge at t=0.

(c) Iteration steps: Repeat steps (a) and (b) periodically with interval T, i.e., activating the reset switch at t=T, t=2T, t=3T, . . . and deactivating it at t=T+Δ, t=2T+Δ, t=3T+Δ, . . . .

(d) Constructing $Q_E(\Delta)$: Use the individual measured values of each interval of step (c) to create the $Q_E(t)-Q_E(0)$ waveform sampled at the frequency 1/T.

Figure 3A:
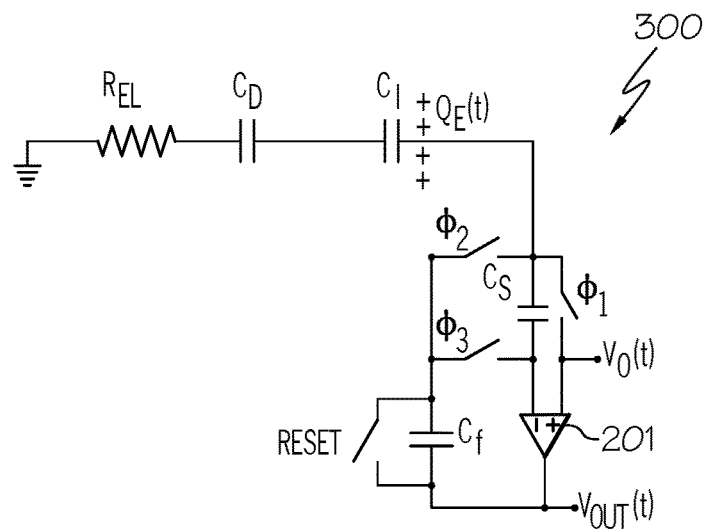
FIG. 3A illustrates the correlated double sampling method to suppress the low frequency noise and offset of the amplifier within the active-electrode sensor in accordance with an embodiment of the present invention.
Figure 3B:
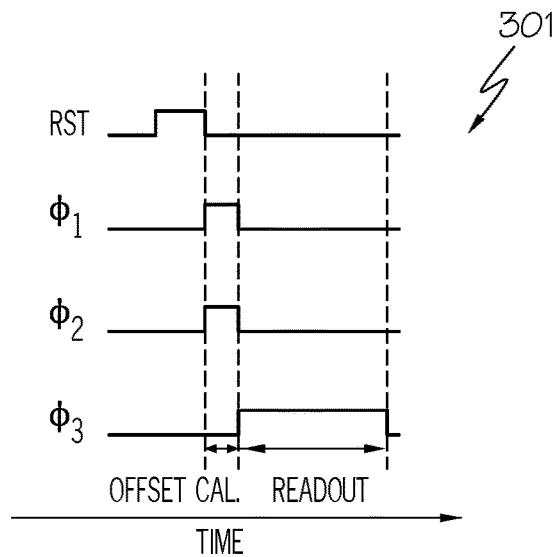
FIG. 3B is a timing diagram of the circuit of FIG. 3A in accordance with an embodiment of the present invention.

The minimum detection level of the active-electrode sensor system is limited by the inherent noise sources within SCCA, particularly the noise contributed by the amplifier. Generally speaking, high-gain amplifiers introduce a high level of low-frequency noise (i.e., 1/f noise) and DC offset in the system. To suppress both the low-frequency noise and offset of the active-electrode sensor, one can use different Correlated Double Sampling (CDS) techniques which are widely used in the art. In FIG. 3A, an exemplary embodiment of circuitry 300 implementing a CDS technique which requires three additional switches activated by signals $\Phi_1$, $\Phi_2$, and $\Phi_3$, and an offset storage capacitor, $C_S$, is shown in accordance with an embodiment of the present invention. As shown in the timing diagram 301 of FIG. 3B, initially the charge across the $C_f$ is reset and subsequently during the offset calibration phase (high $\Phi_1$ and $\Phi_3$), the input referred offset (and noise) of operational amplifier 201 is stored on $C_S$. Finally, in the readout phase, this stored voltage is subtracted from the input of operational amplifier 201 (i.e., the offset and noise are cancelled) and the output becomes independent of this stored value. In this case, A is defined as the duration of time between the rising edge of the reset and the falling edge of $\Phi_3$.

Active-Electrode Biosensor System

Figure 4:
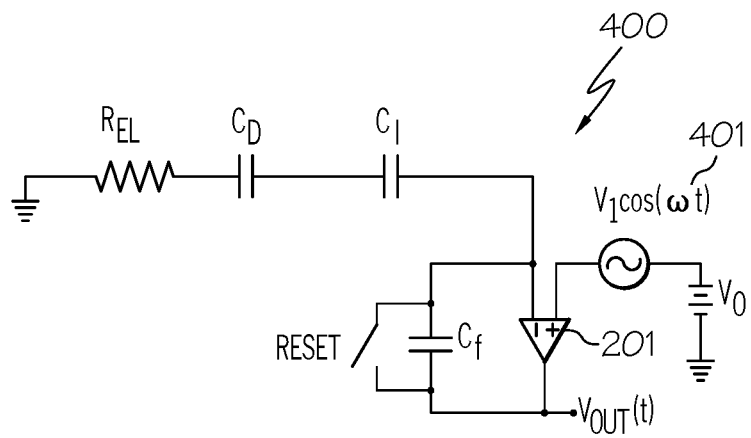
FIG. 4 illustrates using active electrode sensors to measure $C_D$ in accordance with an embodiment of the present invention.

In order to create a biosensor using an active electrode sensor, one should devise methods to couple the measurable $Q_E(t)$ to the biosensing interactions that occur between the target analyte and the recognition layer. There are two general approaches to carry this out this:

Method 1:

The first method is to incorporate the recognition layer within the double layer of the active-electrode system, such that analyte-recognition layer interactions directly affect the distribution of $-Q_E(t)$ and therefore the value of $C_D$. A typical example application for this approach is label-free DNA hybridization detection in which the capturing DNA strands (in the recognition layer) are attached to the solid surface and are physically immobilized within the interface double layer of the active-layer. In this example, successful hybridization of the target charged DNA molecule modifies the interface charge and subsequently the $C_D$. In FIG. 4, it is illustrated how this type of biosensor 400 can be accommodated by the SCCA-based active-electrode sensor in accordance with an embodiment of the present invention. To measure $C_D$, which is an indicator of analyte-recognition layer interactions, one may apply a sinusoidal signal 401 at frequency ω across the interface by applying $V_0(t)=V_0+V_1 \cos(\omega t)$ (both $V_0$ and $V_1$ are constant values) and examine the content of $V_{OUT}(t)$ at frequency ω. In this case, the phase vector of the output, denoted by $V_{OUT}(\omega)$, can be described by the following formula:

$$V_{OUT}(\omega) = V_1 \left[ 1 + \frac{C_D \| C_I}{C_f} \times \frac{1}{1 + j\omega R_{EL} C_D \| C_I} \right] \quad (EQ\ 3)$$

Since $C_f$, $C_I$, and $V_1$ are known values, one can use (EQ 3) and the measurement at a plurality of frequencies to estimate both $C_D$ and $R_{EL}$. By measuring $V_{OUT}(\omega)$ at more than two frequencies, redundant information is created which can be used to further improve the estimated $C_D$ and $R_{EL}$.

Figure 5:
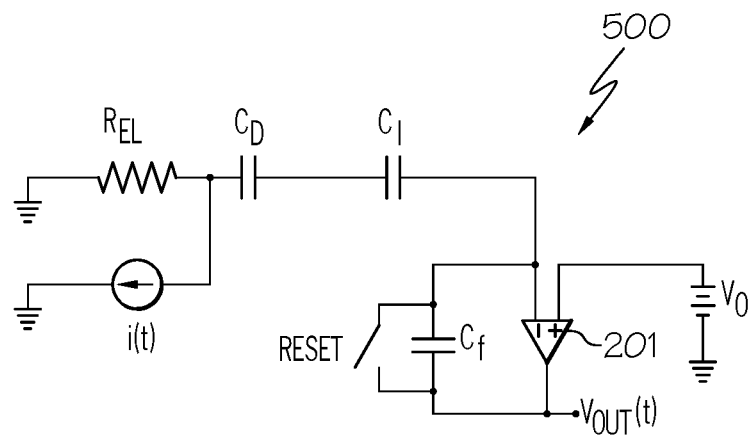
FIG. 5 illustrates using active electrode sensors to measure the ionic currents within the electrolyte in accordance with an embodiment of the present invention.

Method 2:

The second method is to create ionic currents within the biosensing reaction volume (i.e., coordinated where $R_{EL}$ is the dominant electrical element) that are indicative of analyte-recognition layer interactions. An example of such a configuration is common in electrochemical enzyme biosensors which take advantage of electro-active enzymes (e.g., horseradish peroxidase or glucose oxidase) attached to their detection antibody. In FIG. 5, it is illustrated how the active electrode sensor 500 can detect such currents in accordance with an embodiment of the present invention. As illustrated in FIG. 5, i(t), represents the ionic current within the solution which is triggered at t=0. It is straightforward to show that the output of the SCCA in this case, the sensor output for t>0 can be formulated by:

$$V_{OUT}(t) = \frac{e^{\frac{t}{R_{EL}C_D\|C_I}}}{C_f} \int_0^t e^{-\frac{\alpha}{R_{EL}C_D\|C_I}} i(\alpha)\, d\alpha \quad (EQ\ 4)$$

For systems in which i(t) changes occur at a much slower rate compared to the sensor relaxation time, defined by $\tau = R_{EL} C_D \| C_I$, one can simplify and rewrite (EQ 4) as $$V_{OUT}(t) = \frac{R_{EL} C_D \| C_I}{C_f} i(t) \quad (EQ\ 5)$$

One critical issue here is that while (EQ 4) or (EQ 5) offer a means to evaluate i(t) using the SCCA output; however, the exact relationship between these two parameters relies on the values of both $R_{EL}$ and $C_D$ which are known to be susceptible to unwanted drifts during electro-analysis. This is a known and widely-recognized problem in this field. $R_{EL}$ drifts generally happen when the ionic content of the electrolyte is changed (e.g., by injecting in or washing away different reagents), or when the reference electrode remains for a long time in the electrolyte and ages. $C_D$ drifts are often a result of unwanted interaction of the insulator surface with reactants and ions in the electrolyte which slowly alter the charge distribution at the electrolyte-insulator surface. If such drifts are not continually monitored and effectively calibrated out the quality of the measurements will be significantly degraded.

Hybrid Method:

In one embodiment, a method for implementing an active electrode biosensor of the present invention is to concurrently use method 1 and method 2 during electro-analysis. The basic idea is to take advantage of method 1 for continual calibration and monitoring of the surface and electrolyte ($C_D$ and/or $R_{EL}$) and use method 2 to monitor any ionic currents. To enable simultaneous operation of both these methods, one should operate method 1 in frequencies above the Nyquist bandwidth of i(t). For example, if the informative frequency content of i(t) is within DC to 1 kHz, method 1 is operated in frequencies higher than 1 kHz. This approach essentially de-couples the operation of method 1 and method 2 by separating their frequency operation.

Figure 6:
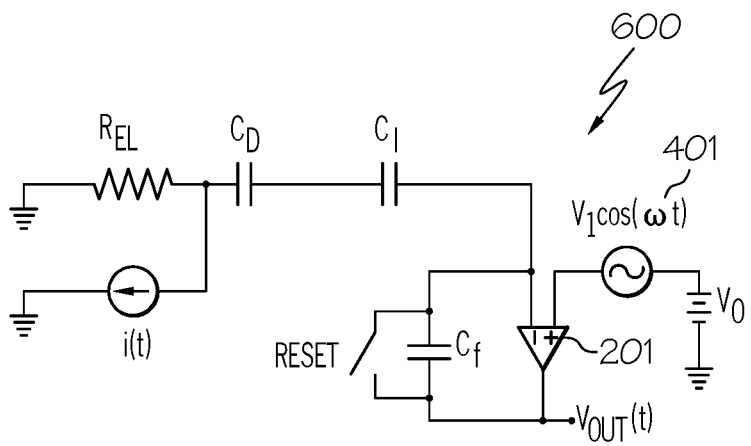
FIG. 6 illustrates hybrid electro-analysis using an active electrode sensor in accordance with an embodiment of the present invention.

In FIG. 6, we illustrate an exemplary embodiment of circuitry 600 as to how the hybrid method can be implemented using the SCCA in accordance with an embodiment of the present invention. The general idea is to use a Low-Pass filter (LPF) and High-Pass Filter (HPF) to isolate the output of each method from $V_{OUT}(t)$ and analyze them independently.

Arrays of Active-Electrode Sensors

In some embodiments, an array of active-electrode sensors are built on a common substrate, such as a semiconductor substrate (e.g., CMOS) and by using VLSI fabrication processes. In some cases, the number of the pixels within this array is greater than 10 and can be as large as $10^8$ per single substrate. Techniques for selecting the row and column of the pixel to be interrogated are widely known to those skilled in the art of design of sensor array and image sensor arrays.

In some situations, a biosensor array includes at least 1, 2, 3, 4, 5, 6, 7, 8, 9, 10, $10^2$, $10^3$, $10^4$, $10^5$, $10^6$, $10^7$, $10^8$, $10^9$, or $10^{10}$ within a cross-sectional area of at most about 1000 $cm^2$, 100 $cm^2$, 10 $cm^2$, 1 $cm^2$, 0.5 $cm^2$, or 0.1 $cm^2$.

In some embodiments in which an array of active-electrode sensors is built in a semiconductor substrate, each pixel may have part of the required circuitry to enable a SSCA-based active electrode sensor, and, for example, the operational amplifier may be shared by a plurality of pixels in, for example, all the pixels within the column. This method of sharing the circuitry in the signal path is a widely used method in CMOS sensor array and image sensor arrays. In some embodiments, the shared circuits are placed in the periphery of the array to minimize the size of the individual pixels.

Detecting DNA Polymerization Using Active-Electrode Biosensors

One of the primary applications that is targeted using the principles of the present invention is DNA sequencing. There are many different techniques to perform DNA sequencing and extract structural information from unknown nucleic acid strands. In some embodiments, DNA sequencing is accomplished via Sequence-by-Synthesis (SBS), in which individual nucleotides (adenine, cytosine, guanine or thymine) are iteratively introduced to a primed DNA complex in the presence of the DNA polymerase enzyme. The occurrence of one or more polymerization events is monitored, such as with the aid of a biochip described herein. Successful polymerization at the 3'-terminus of the primer is indicative of the presence of the complementary base on the template DNA while the amplitude of the polymerization is indicative of the number of consecutive identical bases. Different approaches have been provided for detecting the polymerization events and perform SBS. Examples are bioluminescence-based enzymatic cascade (e.g., J. M. Rothberg and J. H. Leamon, "The development and impact of 454 sequencing", Nature Biotech., vol. 23, no. 10, pp. 1117-1125, 2008), fluorescent-label nucleotides (e.g., U.S. Pat. No. 7,835,871), and pH-based (e.g., U.S. Pat. No. 7,948,015). In the present invention, an alternative electrochemical technique is provided which is not only amendable to integration and miniaturization, but also offers a significantly better noise performance and measurement robustness.

In the following, the details of how SBS can be enabled by the active electrode biosensors are described. Initially, the electronic characteristics of DNA polymerization, where its detection is fundamental in SBS, is discussed followed by discussing the multiple embodiments in which DNA polymerization can be detected using the active-electrode biosensors.

In DNA polymerization, the 3'-terminus of the primer is extended by the DNA polymerase enzyme which facilitates the incorporation of individual nucleotides (deoxyribonucleotide triphosphates, dNTPs) that are complementary to the template DNA strand. A single nucleotide incorporation event that extends the primer from length n to n+1 is best described by

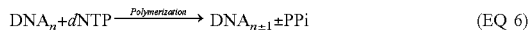

$$DNA_n + dNTP \xrightarrow{Polymerization} DNA_{n\pm 1} \pm PPi \quad (EQ\ 6)$$

which states that the DNA-enzyme complex absorbs a single dNTP molecule and releases a pyrophosphate (PPi) molecule. Since all of the participating molecules in the catalytic reaction of (EQ 6) (including both the substrates and products) are essentially charged species, it is feasible to setup certain conditions in which DNA polymerization can result in a measurable electronic parameter in this system. If this is done, then monitoring this particular parameter can be used to detect (and quantify) DNA polymerization and therefore can be used to perform SBS. All of the DNA sequencing embodiments described herein operate according to this particular principle.

Previously, Sakurai et al. ("Real-Time Monitoring of DNA Polymerase Reactions by a Micro ISFET pH Sensor", Anal. Chem, vol. 64, pp. 1996-1997, 1992) demonstrated that a small pH change induced by dNTP incorporation can be detected by a micro ISFET pH sensor and used, in real-time, to detect DNA polymerization events. Later, Pourmand et al., ("Direct electrical detection of DNA synthesis", PNAS, vol. 102, no. 17, pp. 6866-6870, 2006) suggested that the transient electrical signal generated by DNA immobilized on a polarized gold electrode during polymerization can be sensed in real-time using differential voltage and current amplifiers and be used to sense dNTP incorporations. Recently, Rothberg et al., ("An integrated semiconductor device enabling non-optical genome sequencing", Nature, vol. 475, pp. 348-352, 2011) demonstrated how an array of ISFET in conjunction with random bead arrays can be used to create high-throughput parallel pH-based SBS arrays.

In the present invention, an alternative approach is introduced which uses embodiments of an active-electrode sensor to detect DNA polymerization to enable DNA SBS. The premise of this system is the fact that nucleotide incorporation when the primed DNA is immobilized (i.e., is attached to a solid surface), can result in an imbalance between the absorbed and released free ionic charges in the electrolyte near the DNA, which in turn results in localized ionic currents that can be sensed by the active-electrode biosensor. Unlike the previously reported system, active-electrode arrays, rely neither on the concentration of protons and ISFET structures, nor polarized gold electrodes to detect polymerization. In addition, active-electrode sensors can also measure the surface capacitance concurrently with polymerization detection (Hybrid method), a unique feature that none of the aforementioned references have.

Figure 7:
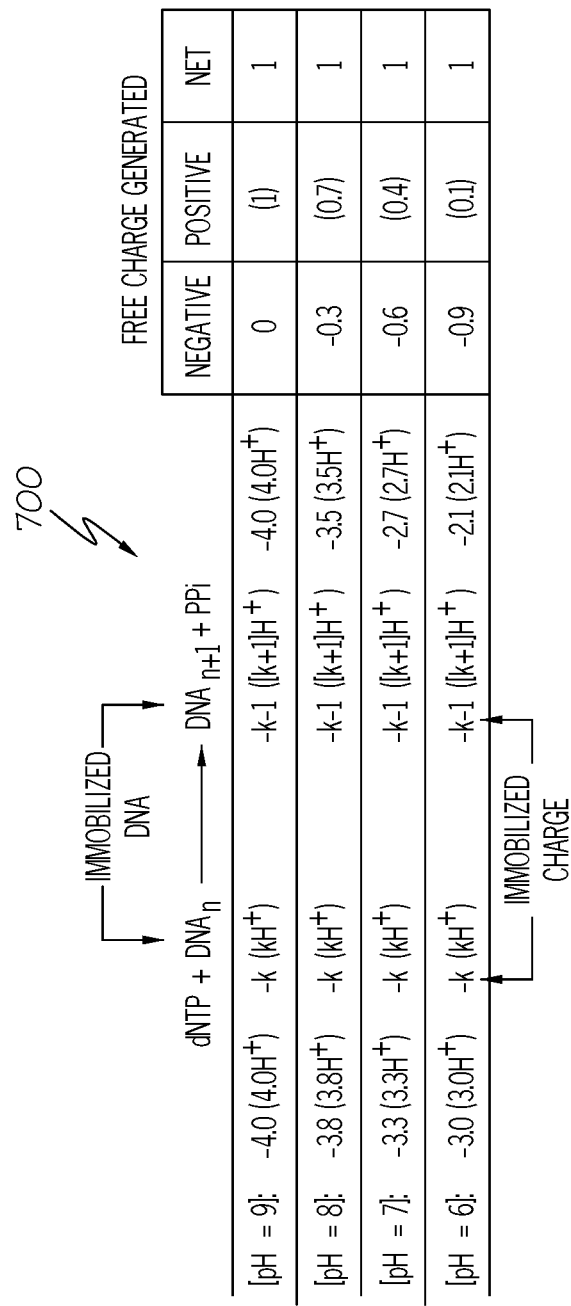
FIG. 7 is a table illustrating the absorbed ions and net free charge generated during a single nucleotide incorporation at different pH levels in accordance with an embodiment of the present invention.

Referring now to FIG. 7, FIG. 7 is a table 700 illustrating the ionic species and the generated net free charge of a single nucleotide incorporation event when DNA is immobilized in accordance with an embodiment of the present invention. As illustrated in FIG. 7, depending on the pH of the electrolyte and isoelectric characteristics of the involved molecules, the generated average net free negative charge (from PPi) and net free positive charge (from protons, $H^+$) are different. Yet, the net generated charge (i.e., the sum of the positive and negative charges) is always positive and equal to +1. This indicates that DNA polymerization always creates a positive diffusion potential in the electrolyte at the DNA polymerization coordinate which in turn can create an outward going ionic current through free net charge diffusive spreading.

Based on this observation, one can state that if an active-electrode biosensor is placed in the electrolyte such that it measures the ionic current that is generated by DNA polymerization, one can detect DNA polymerization events. It is important to realize that the DNA itself does not have to be in intimate proximity of the electrode and as long as the current reaches the electrode, one can detect polymerization. In practice this means that the electrolyte-insulator surface should be within a few diffusion lengths for the PPi and proton ions, which is defined by the average distance that these ions can move the DNA polymerization until they recombine with other ions in the solution. Depending on the characteristics of the solution (e.g., salt concentration, buffer capacity and temperature), this distance is typically between 1 nm and 10 nm.

It is noted herein that the embodiments of the present invention are categorically different from all ISFET-based sensors described in the art. ISFET devices and sensors implemented by them, by their definition, include electrically-floating electrodes where the electrode potential is undefined (unlike active-electrode sensors which are always set to $V_O(t)$) and can (and should) change during measurements. In addition, unlike Pourmand et. at and its derivatives, active-electrode sensors described herein do not use clamp or voltage amplifiers and furthermore do not require the DNA to be attached to the polarized metal electrode surface to ensure that the DNA backbone protonization is directly shielded by the electrode.

In some embodiments, the components and procedures to detect DNA polymerization using active electrode biosensors are:

(a) Immobilize a plurality of identical primed DNA molecules in a reaction chamber and interface an active-electrode biosensor system to it;

(b) Introduce dNTPs into the reaction chamber in presence of the DNA polymerase enzyme;

(c) Measure in real-time the ionic current, $R_{EL}$, and $C_D$ using the aforementioned hybrid biosensing method;

(d) Estimate i(t) by using the measured $V_{OUT}(t)$, $R_{EL}$, and $C_D$; and (e) Use the estimated i(t) to identify the occurrence and amount of DNA polymerization events for the primed DNA molecules interfaced to the active-electrode biosensor.

In some embodiments, to carryout a DNA SBS procedure and identify the sequence of primed DNA molecules (e.g., a clonal population thereof), the following steps are used:

(a) Immobilize a plurality of identical primed DNA molecules in a reaction chamber and interface an active-electrode biosensor system to it;

(b) Introduce a single type of nucleotide (dATP, dTTP, dCTP, or dGTP) in the presence of DNA polymerase and monitor DNA polymerization;

(c) Remove the remaining unreacted nucleotides from the reaction chamber;

(d) Repeat step (b) through (c) for a different nucleotide; and (e) Use the occurrence and the quantity of DNA polymerization events to find the sequence.

In the embodiments of the present invention where the integrated active-electrode biochip array can carries parallel (multiplexed) DNA sequencing, one has:

(a) An immobilized primed DNA array created on the surface of a CMOS-integrated semiconductor chip where identical DNA strands are located in distinct coordinates within the array, referred to herein as the pixels;

(b) An array of active-electrode biosensors built in a CMOS chip in the form of an integrated circuit in which individual pixels of the DNA array have one active-electrode biosensor;

(c) A reaction chamber which can contain aqueous solutions on top of the CMOS chip where the DNA array is located;

(d) A fluidic single-directional flow-through system which enables controlled injection and removal of different aqueous from the reaction chamber including, but not limited to, dNTPs, DNA polymerase enzyme, wash buffer, dNTPase, and pH standard buffers;

(e) A system to monitor and control the temperature of the reaction chamber; and (f) A data acquisition and processing device which can extract, read, and process the output of each integrated active electrode biosensor.

Preparing DNA for Sequencing

The nucleic acid being sequenced is referred to herein as the target nucleic acid. Target nucleic acids include, but are not limited to, DNA, such as but not limited to, genomic DNA, mitochondrial DNA, cDNA and the like, and RNA, such as but not limited to, mRNA, miRNA, and the like. The nucleic acid may be from any source including naturally occurring sources or synthetic sources. The nucleic acids may be Polymerase Chain Reaction (PCR) products, cosmids, plasmids, naturally occurring or synthetic libraries, and the like. The present invention is not to be limited in this regard. The methods provided herein can be used to sequence nucleic acids of any length. The following is a brief description of examples of these methods.

In some embodiments, target nucleic acids are prepared using any manner known in the art. As an example, genomic DNA may be harvested from a sample according to techniques known in the art (see for example Sambrook et al. "Maniatis"). Following harvest, the DNA may be fragmented to yield nucleic acids of smaller length. The resulting fragments may be on the order of hundreds, thousands, or tens of thousands nucleotides in length. In some embodiments, the fragments are 200-1000 base pairs (bp) in size, or 300-800 by in size, although they are not so limited. Nucleic acids may be fragmented by any means including but not limited to mechanical, enzymatic or chemical means. Examples include shearing, sonication, nebulization and endonuclease (e.g., Dnase I) digestion, or any other technique known in the art to produce nucleic acid fragments, optionally of a desired length. Fragmentation can be followed by size selection techniques which can be used to enrich or isolate fragments of a particular length or size. Such techniques are also known in the art and include, but are not limited to, gel electrophoresis or Solid-Phase Reversible Immobilization (SPRI).

In some embodiments, the size selected target nucleic acids are ligated to adaptor sequences on both the 5' and 3' ends. These adaptor sequences comprise amplification primer sequences to be used in amplifying the target nucleic acids. One adaptor sequence may also comprise a sequence complementary to the sequencing primer. The opposite adaptor sequence may comprise a moiety that facilitates binding of the nucleic acid to a solid support, such as but not limited to, a bead. An example of such a moiety is a biotin molecule (or a double biotin moiety, as described by Diehl et al. *Nature Methods,* 2006, 3(7):551-559) and such a labeled nucleic acid can therefore be bound to a solid support having avidin or streptavidin groups. The resulting nucleic acid is referred to herein as a template nucleic acid. The template nucleic acid comprises at least the target nucleic acid and usually comprises nucleotide sequences in addition to the target.

Immobilization of DNA

There are different known methods in the art that one can use to immobilize primed DNA strands near an on the active-electrode biosensor. FIGS. 8A-8C illustrates different embodiments for immobilizing clonal DNA in proximity of an active electrode in accordance with an embodiment of the present invention. Referring to FIGS. 8A-8C, FIGS. 8A-8C illustrate how identical DNA strands 801 are physically placed near the integrated active biosensors that are embedded in a CMOS chip 802 (includes a silicon substrate 809 and metal layers 810). In one embodiment, DNA strands 801 are immobilized within microwell structures 803 covalently using linkers or through base pairing (hybridization) on the surface of functionalized micro-beads 804, active electrodes 805, or porous polymers 806, referred to as solid support herein. In alternative embodiments, microwell structure 803 may not be present and DNA strands 801 are immobilized covalently using linkers, or through base pairing (hybridization) on the surface of the electrolyte-insulator interface 807 (insulator identified as element 808), or porous polymers 806. The size of the pixels (parameter X) is preferably between 0.1 μm to 50 μm, while the aspect ratio of individual microwells 803 (i.e., X/Y) varies between 0.6 to 3.

In some embodiments, a linker (or spacer) is specifically used to distance the template nucleic acid (and in particular the target nucleic acid sequence comprised therein) from the solid support. This can facilitate sequencing of the end of the target closest to the surface. Examples of suitable linkers are known in the art (see Diehl et al. *Nature Methods*, 2006, 3(7):551-559) and include, but are not limited to, carbon-carbon linkers, such as, but not limited to, iSp18.

The beads used in the present invention can be made of any material including, but not limited to, cellulose, cellulose derivatives, gelatin, acrylic resins, glass, silica gels, PolyVinyl Pyrrolidine (PVP), co-polymers of vinyl and acrylamide, polystyrene, polystyrene cross-linked with divinylbenzene or the like (see, Merrifield Biochemistry 1964, 3, 1385-1390), polyacrylamides, latex gels, dextran, cross-linked dextrans (e.g., Sephadex™), rubber, silicon, plastics, nitrocellulose, natural sponges, metal, and agarose gel (e.g., Sepharose™). In one embodiment, the beads are streptavidin-coated beads. The bead diameter can depend on the density of the well array used with larger arrays (and thus smaller sized wells) requiring smaller beads. Generally, the bead size may be about 0.1 μm-10 μm, or 1 μm-5 μm. In an example, the beads are about 5.91 μm in diameter. In another example, the beads are about 2.8 μm in diameter. It is to be understood that the beads may or may not be perfectly spherical in shape. It is to be understood that other beads may be used and other mechanisms for attaching the nucleic acid to the beads may be utilized.

In some embodiments, a homogeneous population of amplified nucleic acids is conjugated to one or more beads with the proviso that each bead will ultimately be bound to a plurality of identical nucleic acid sequences. The degree of loading of nucleic acid templates onto beads will depend on a number of factors including the bead size and the length of the nucleic acid. In most aspects, maximal loading of the beads is desired. Amplification and conjugation of nucleic acids to solid support, such as beads, may be accomplished in a number of ways, including, but not limited to, emulsion PCR as described by Margulies et al. *Nature* 2005 437(15): 376-380 and accompanying supplemental materials. In some embodiments, the amplification is a representative amplification. A representative amplification is an amplification that does not alter the relative representation of any nucleic acid species.

Before and/or while in the wells of the flow chamber, the beads are incubated with a sequencing primer that binds to its complementary sequence located on the 3' end of the template nucleic acid (i.e., either in the amplification primer sequence or in another adaptor sequence ligated to the 3' end of the target nucleic acid) and with a polymerase for a time and under conditions that promote hybridization of the primer to its complementary sequence and that promote binding of the polymerase to the template nucleic acid. The primer can be of virtually any sequence provided it is long enough to be unique. The hybridization conditions are such that the primer will hybridize to only its true complement on the 3' end of the template. Suitable conditions are disclosed in Margulies et al. *Nature* 2005 437(15):376-380 and accompanying supplemental materials.

Reaction Temperature

The sequencing reaction can be run at a range of temperatures. Typically, the reaction is run in the range of 30-60° C., 35-55° C., or 40-45° C. In some embodiments, it is preferable to run the reaction at temperatures that prevent formation of a secondary structure in the nucleic acid. However, this is balanced with the binding of the primer (and the newly synthesized strand) to the template nucleic acid and the reduced half-life of Pyrophosphatase at higher temperatures. In one embodiment, a suitable temperature is about 41° C. The solutions including the wash buffers and the dNTP solutions are generally warmed to these temperatures in order not to alter the temperature in the wells. The wash buffer containing Pyrophosphatase, however, is preferably maintained at a lower temperature in order to extend the half-life of the enzyme. Typically, this solution is maintained at about 4-15° C., and more preferably at about 4-10° C.

Electrode Fabrication

Figure 9A:
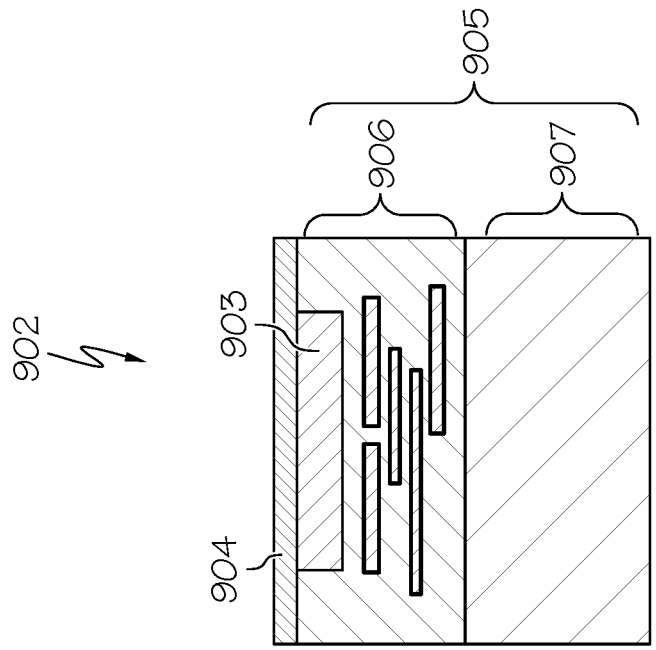
FIGS. 9A-9B illustrate examples of CMOS-integrated sensing electrodes in accordance with an embodiment of the present invention.
Figure 9B:
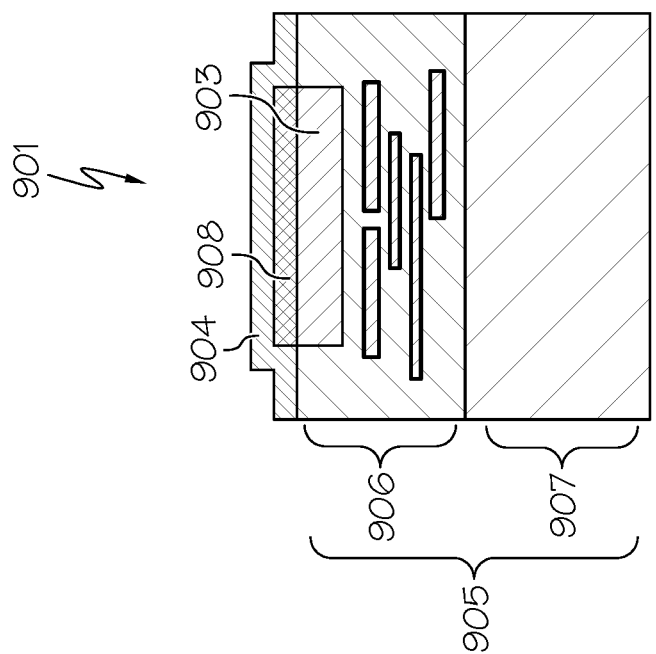

Referring now to FIGS. 9A-9B, FIGS. 9A-9B illustrate exemplary CMOS-integrated sensing electrodes 901, 902 in accordance with an embodiment of the present invention. The metal of choice in Integrated Circuits (ICs) is generally aluminum with certain amount of impurities. Accordingly, in the CMOS-integrated embodiments of the present invention, one may use aluminum metal layers 903 as the active electrode. The top metal layer in CMOS-integrated sensing electrode 901, 902 is the optimal metal layer since it is the closest to the surface of the chip which can be coupled to the DNA array. The metal layer in CMOS-integrated sensing electrode 901 is generally covered by a thick passivation layer (typically made of durable oxides such as $SiO_2$ and $Si_3N_4$) to protect the metal chemically and mechanically from the external environment. Neither bare aluminum nor aluminum covered by a thick dielectric layer is an optimal embodiment for the sensing electrode of active-electrode biosensors. As a result, an insulating layer 904 should be formed. The sensing electrodes 901, 902 of the present invention in are formed by first creating openings in the passivation layer of the CMOS chip 905 (comprised of metal layers 906 and silicon substrate 907) and exposing the top metal layer. In one embodiment, the top metal is subsequently covered by a blanket layer of an insulator 904 (thickness varies between 5 nm to 2 μm) using conventional thin-film oxide deposition techniques and the microwells (if any) will be created on its top. Example materials include $SiO_2$, $Ti_3N_4$, $Si_3N_4$, $TiO_2$, $Al_2O_3$, and $HfO_2$. The oxide or nitride layer can be formed by various deposition techniques, such as Chemical Vapor Deposition (CVD), Atomic Layer Deposition (ALD), or Physical Vapor Deposition (PVD, such as, e.g., sputtering). In alternative embodiments, a noble metal layer 908 (e.g., Pt or Au) is first deposited over the exposed metal by using conventional thin-film metal deposition techniques (e.g., evaporation or electroplating), and afterwards, the blanket oxide layer is placed on top of it. In one embodiment, the thickness of noble layer 908 can vary between 5 nm to 1 μm.

Integration and SBS Arrays

In a preferred DNA SBS embodiment of the present invention, the active-electrode biosensor array is built on the semiconductor substrate of a CMOS process fabricated using VLSI fabrication processes. In some cases, the number of the pixels within this array is greater than 10 and can be as large as $10^8$ per single substrate. Integrated circuit design techniques for selecting the row and column of the pixel to be interrogated are widely known to those skilled in the art in the design of CMOS sensor arrays and image sensor arrays.

In some situations, the SBS array includes at least 1, 2, 3, 4, 5, 6, 7, 8, 9, 10, $10^2$, $10^3$, $10^4$, $10^5$, $10^6$, $10^7$, $10^8$, $10^9$, or $10^{10}$ within a cross-sectional area of at most about 1000 cm$^2$, 100 cm$^2$, 10 cm$^2$, 1 cm$^2$, 0.5 cm$^2$, or 0.1 cm$^2$.

In some embodiments in which a SBA array is built in a semiconductor substrate, each biosensing pixel may have part of the required circuitry to enable a SSCA-based active electrode biosensing, and, for example, the operational amplifier may be shared by a plurality of pixels in, for example, all the pixels within a column of the array. This method of sharing the circuitry in the signal path is a widely used method in CMOS sensor arrays and image sensor arrays. In preferred embodiments, the shared circuits are placed in the periphery of the SBS array to minimize the size of individual biosensing pixels.

EXAMPLE EMBODIMENT

In this section, it is described herein an exemplary embodiment of the present invention. This system has been successfully reduced to practice using the 0.18 μm CMOS fabrication process offered by Taiwan Semiconductor Manufacturing Company (TSMC). It is noted for clarity that the principles of the preset invention are not to be limited in scope (such as the scope of its applications) to the below described details of this embodiment.

Figure 10B:
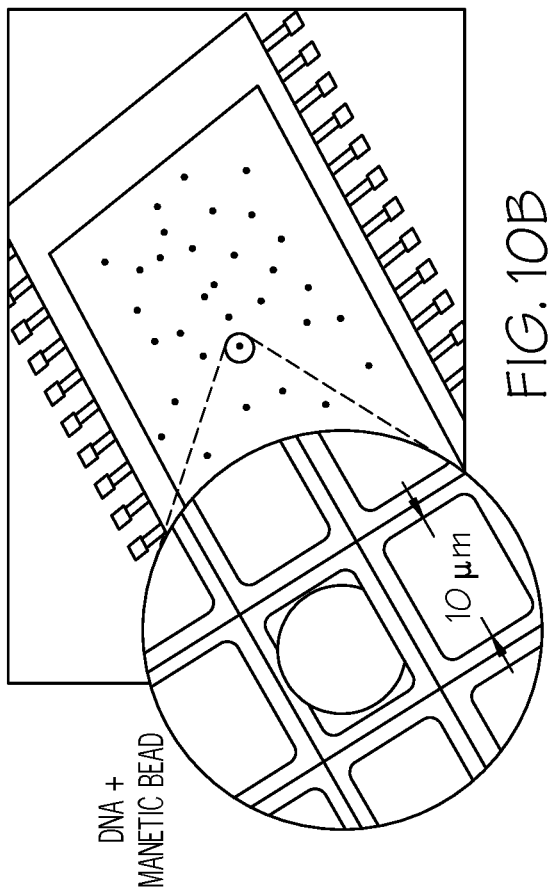
FIGS. 10A-10C illustrate an integrated active electrode DNA sequencing biochip and the basic layer structure of its pixels in accordance with an embodiment of the present invention.
Figure 10A:
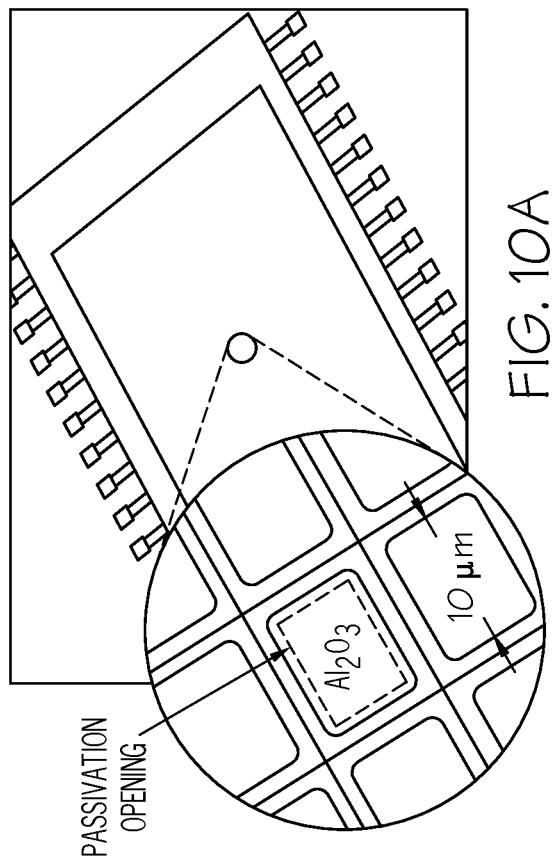
Figure 10C:
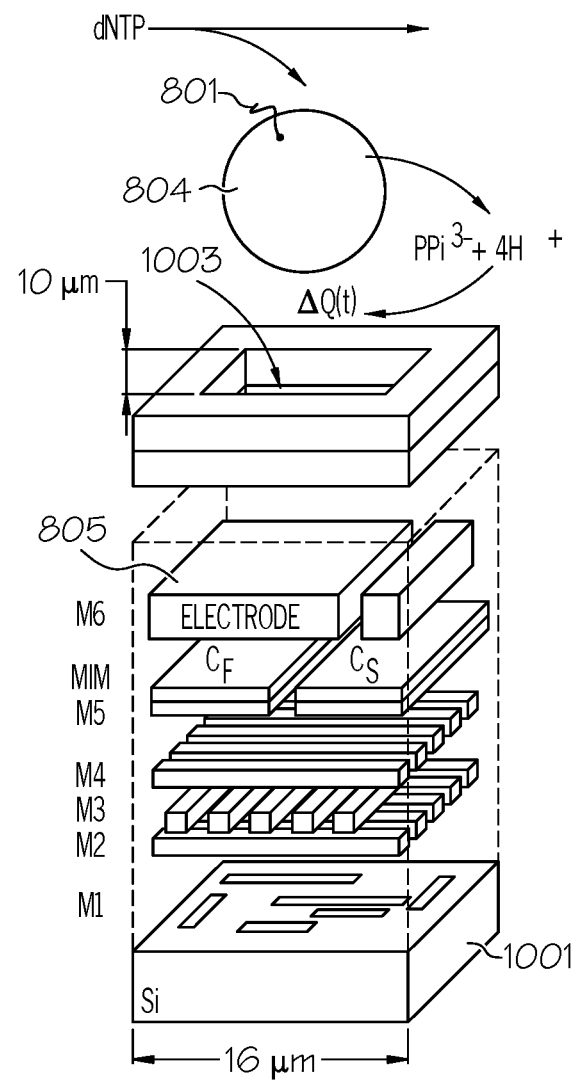

Referring now to FIGS. 10A-10C, FIGS. 10A-10C illustrate an integrated active electrode DNA sequencing biochip and the basic layer structures of its pixels in accordance with an embodiment of the present invention. Specifically, referring to FIGS. 10A-10C in conjunction with FIGS. 8A-8C, FIGS. 10A-10C illustrate the basic structure of the active-electrode CMOS DNA sequencing biochip and further illustrates the scanning electron microscope image of the CMOS chip surface with and without DNA-bead complexes. Each pixel 1001 is 16 μm×16 μm and the total array size is 90×90. The electrode (layer M6) 805 is made of aluminum and the insulating layer is aluminum oxide (Al$_2$O$_3$). Each pixel 1001 has a shallow microwell (Y=2 μm) built on its top with a 10 μm×10 μm openings 1003 to hold a single 10 μm bead 804, on which DNA strands 801 are immobilized. In this CMOS process, 6 metal layers (M1-M6) are used and the capacitors, required for SCCA operation, are created using the metal-insulator-metal (MIM) layers that are offered in this CMOS process.

Figures 11A, 11B:
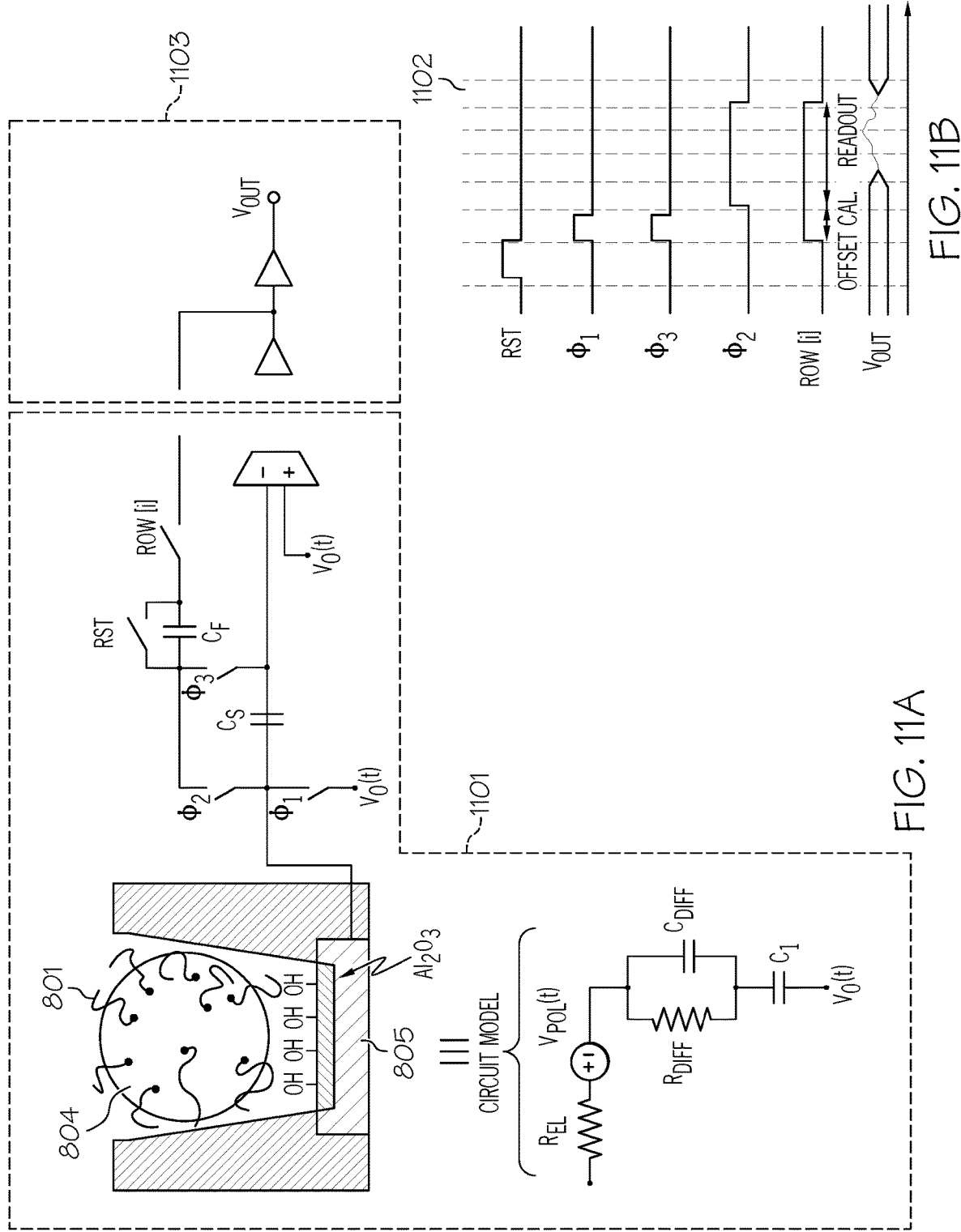
FIG. 11A illustrates the general architecture of the CMOS-integrated active-electrode biosensor pixel for DNA sequencing in accordance with an embodiment of the present invention.
FIG. 11B is a timing diagram of in-pixel and out-of-pixel in accordance with an embodiment of the present invention.

Referring now to FIGS. 11A-11B, FIG. 11A illustrates the general architecture of the CMOS-integrated active-electrode biosensor pixel 1101 for DNA sequencing in accordance with an embodiment of the present invention and FIG. 11B is a timing diagram 1102 of in-pixel 1101 and out-of-pixel 1103. The goal is to measure i(t) by implementing a SSCA with CDS to reduce the effect of amplifier 1/f noise and offset. The negative feedback of the amplifier keeps the electrode potential constant and equal to $V_0(t)$ at all times. The main capacitors in this topology are the feedback capacitor ($C_F$=90 fF), the offset storing capacitor ($C_S$=105 fF), and the electrode-electrolyte interface capacitor (1 pF<$C_1$∥$C_D$<10 pF).

Figure 12:
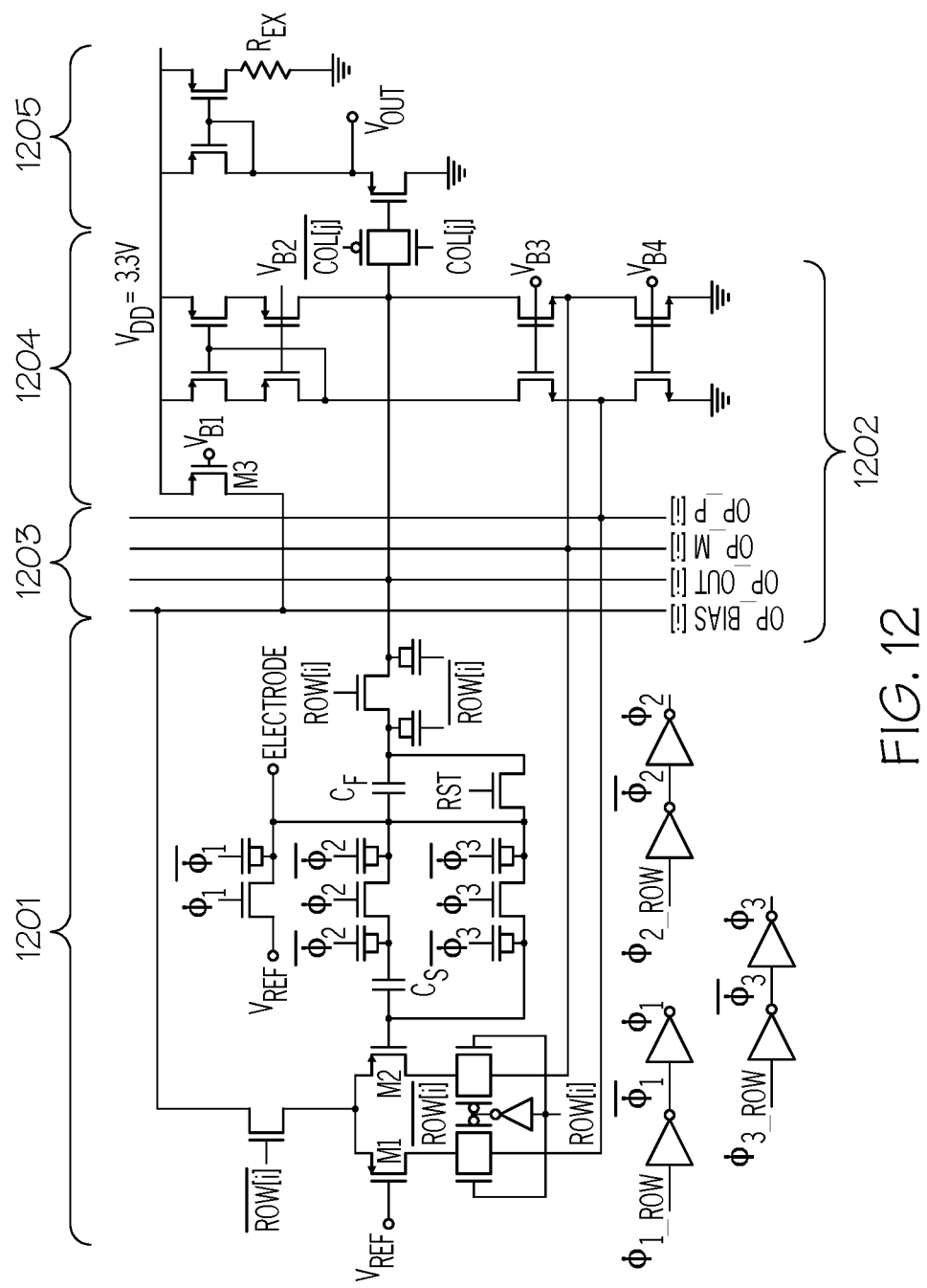
FIG. 12 is a transistor-level schematic of a signal chain in accordance with an embodiment of the present invention.

FIG. 12 illustrates the transistor-level schematic of the signal chain in accordance with an embodiment of the present invention. Referring now to FIG. 12, during the calibration phase, the amplifier offset is stored onto $C_S$. Subsequently during the readout phase, the voltage stored on $C_S$ cancels the offset and low frequency fluctuations while reducing the amplifier gain error.

In order to minimize the pixel circuitry, only the switches and the differential pair (M1 and M2) of the SCCA are integrated in-pixel (pixel (i,j)) 1201 as shown in FIG. 12. The rest of the transistors including the tail current source (M3) are shared at the column level 1202 (comprised of column analog bus (column (j) analog bus) 1203 and column amplifier (column (j) amplifier) 1204. Both $C_F$ and $C_S$ are MIM capacitors and are placed on top of the active circuitry and below the sensing electrode (see FIGS. 10A-10C). During readout, the i$^{th}$ row of the array is activated by ROW[i], which connects the circuitry in the column to the pixel. The outputs of the SCCAs are available at the column level and are multiplexed to provide a single buffered output 1205 for the chip. The total consumed power in this chip is approximately 13 mW using a 3.3V supply.

Figure 13A:
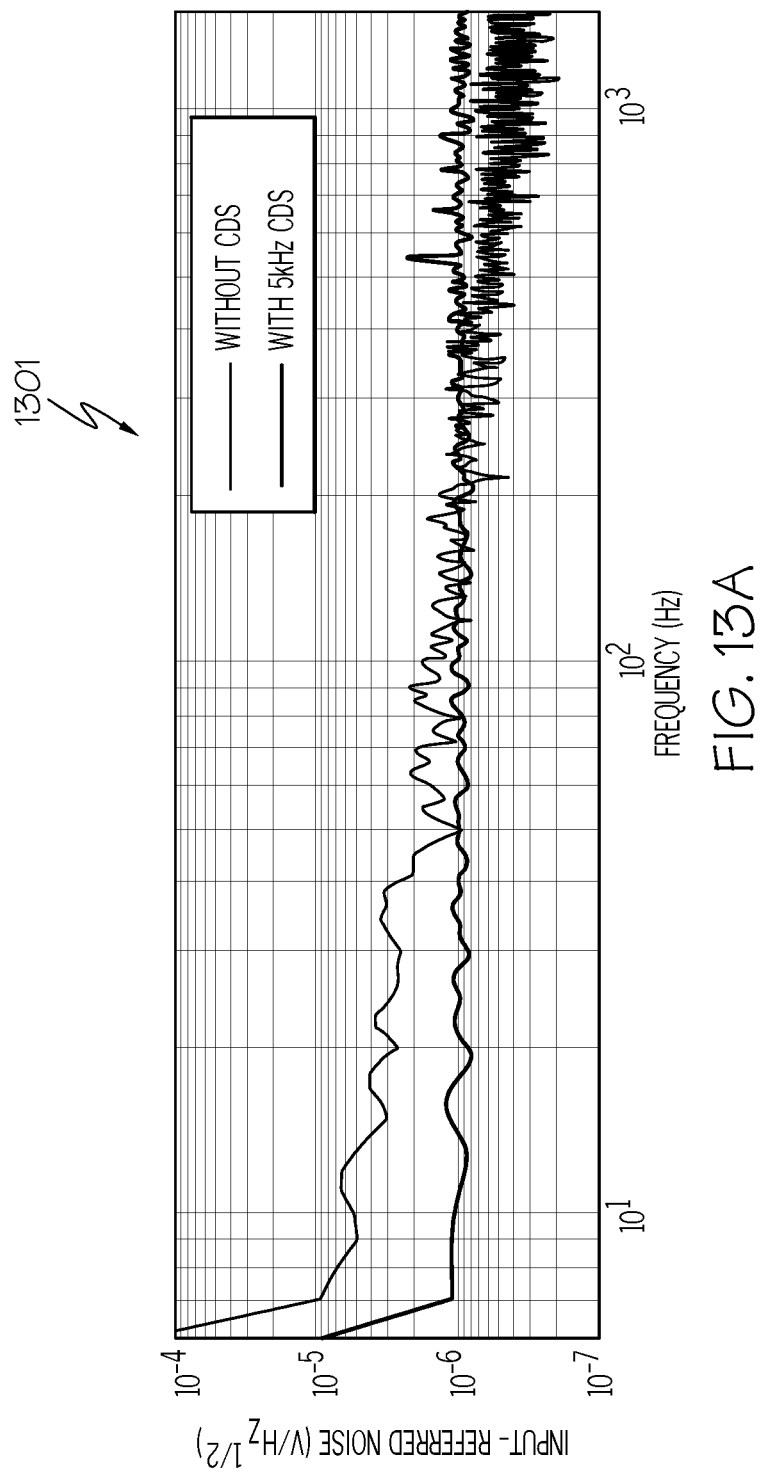
FIGS. 13A-13C are graphs illustrating electrical detection performances in accordance with an embodiment of the present invention.
Figure 13B:
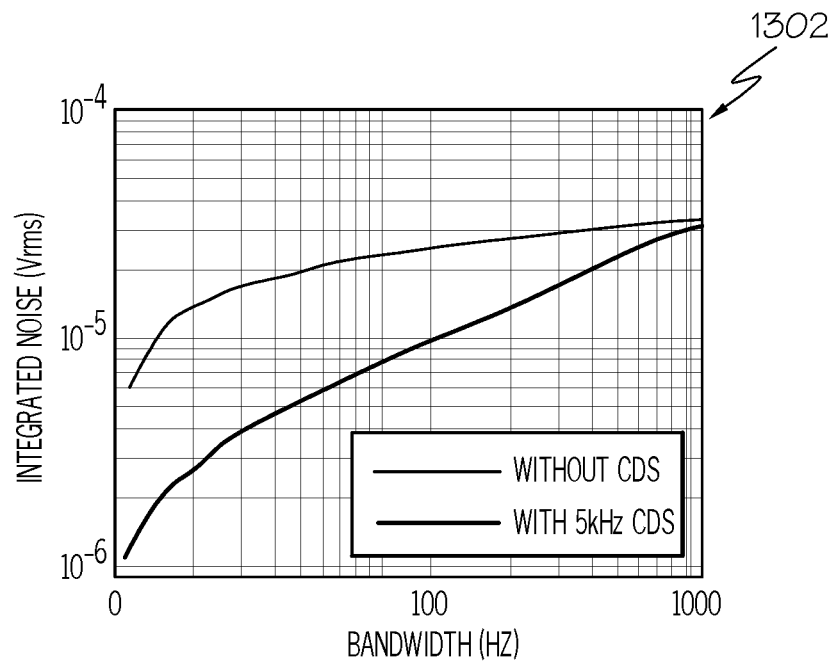
Figure 13C:
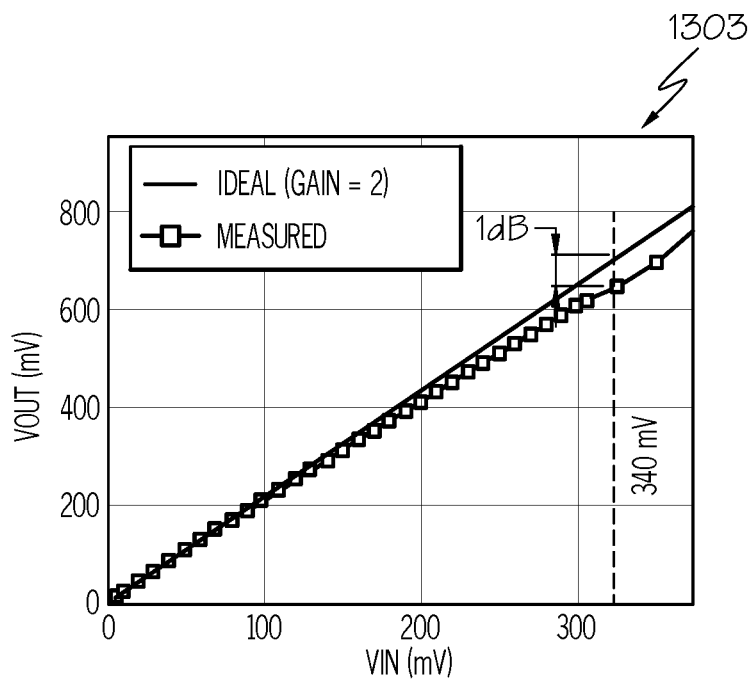

FIGS. 13A-13C illustrates the electrical performance of the SCCAs in accordance with an embodiment of the present invention. FIG. 13A includes a graph 1301 depicting the frequency versus the input-referred noise. FIG. 13B includes a graph 1302 depicting the bandwidth versus integrated noise and FIG. 13C includes a graph 1303 depicting the input voltage ($V_{IN}$) and the output voltage ($V_{OUT}$). In the frequencies below 10 kHz, the noise power spectral density (PSD) is dominated by 1/f noise of the operational amplifier which can be suppressed by CDS. As evident, by using a 5 kHz CDS, the input-referred noise can be suppressed to ~10 μVrms for a 100 Hz bandwidth. The 1 dB compression point for this amplifier measured at a gain of two is 340 mV which corresponds to a detection dynamic range of 90 dB.

Figure 14A:
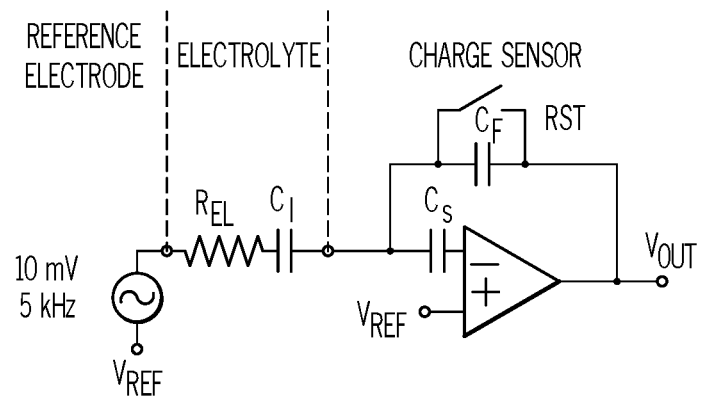
Figure 14B:
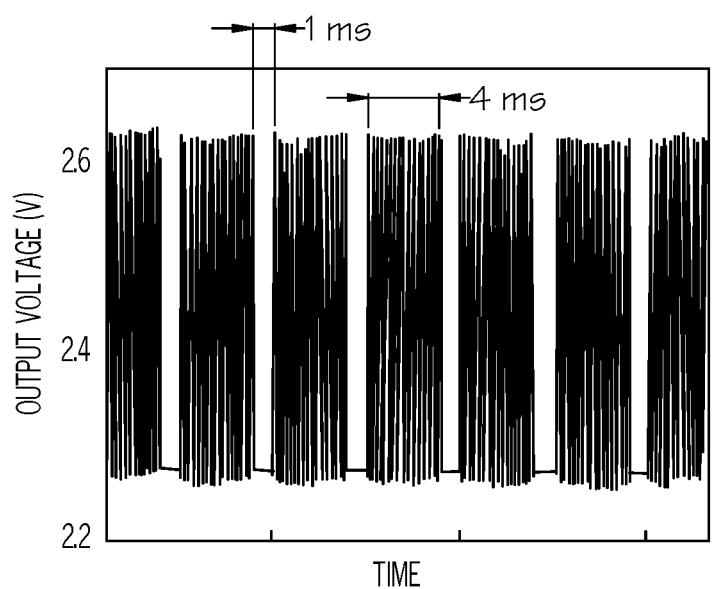

FIGS. 14A-14C illustrate the interface capacitance measurements versus the solution pH in graph 1400 in accordance with an embodiment of the present invention. Referring to FIG. 14C, FIG. 14C provides the $C_D$∥$C_1$ measurement as the solution pH is changed. As illustrated in FIG. 14A, a 10 mV amplitude sinusoidal voltage with a frequency of 5 kHz is applied to the reference electrode immersed in the solution. The generated $V_{OUT}$(t) (FIG. 14B) is then used to evaluate the SCCA gain and subsequently $C_D$∥$C_1$.

Figure 15A:
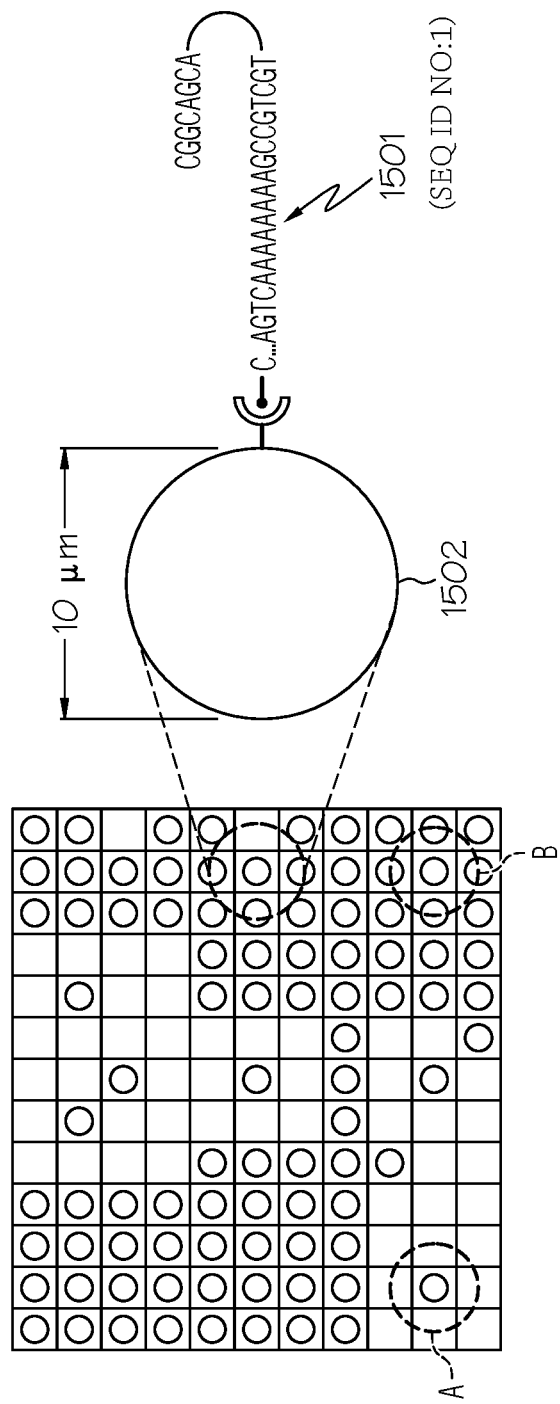

FIGS. 15A-15C illustrate the DNA polymerization detection in accordance with an embodiment of the present invention. Referring now to FIGS. 15A-15C, FIG. 15C provides the measurement results of real-time DNA polymerization detection. In this experiment, as shown in FIG. 15A, self-primed biotinylated DNA strands 1501 (SEQ ID NO:1) are immobilized on streptavidin coated magnetic beads 1502. Deoxynucleotide triphosphates (dATP, dCTP, dGTP, and dTTP nucleotides) 1503 are added sequentially to trigger polymerization and perform SBS as shown in FIG. 15B. As is evident in the experimental results as shown in FIG. 15C, the measured transient current is large (in the order of 100 s of fA) only when the correct nucleotide is added (dTTP 1504 in this case) and negligible change can be observed during the control experiment when the unmatched nucleotides (dATTP, dCTP, and dGTP) are introduced into the solution.

Figure 16:
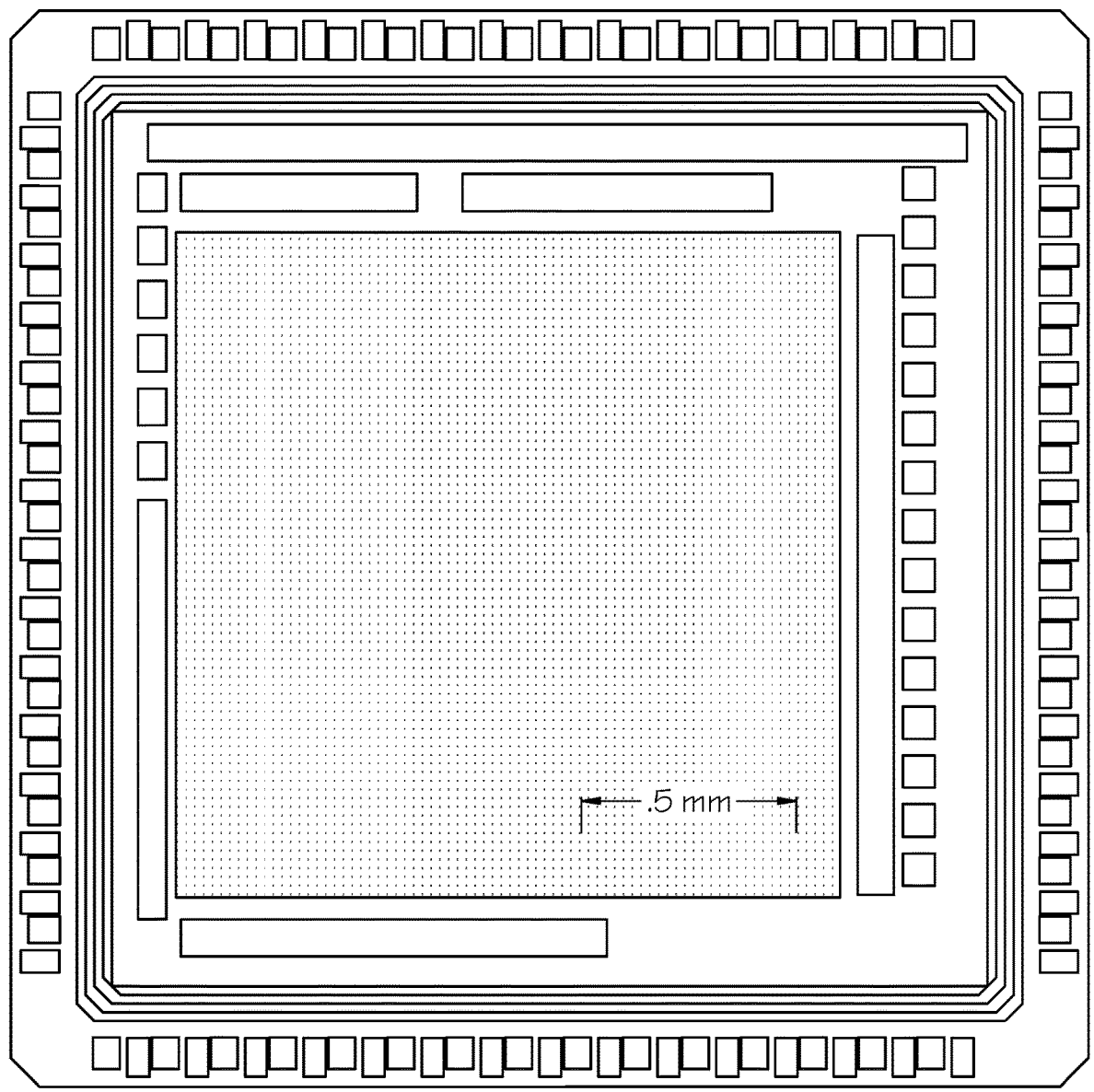
FIG. 16 is a micrograph of the active-electrode CMOS biochip for DNA sequencing in accordance with an embodiment of the present invention.

FIG. 16 illustrates the micrograph of the active-electrode CMOS biochip for DNA SBS in accordance with an embodiment of the present invention. As illustrated in FIG. 16, the 90×90 sensor array is placed in the middle of the chip and the electronic input-output (I/O) of the chip is taken at the periphery. The total chip size is 2.5 mm×2.5 mm.

The experimental protocol for the measurements is:

Reagents:

Biotinylated ss-DNA strand (5'-Biotin-CCTCTGAGT-CAAAAAA AAGCCGTCGTTATACAACGGAACGTTGTATAAC-GACGGC-3') from Integrated DNA Technologies (IDT), USA; Streptavidin coated magnetic beads of size 8-10 μm from Spherotech, USA; DNA polymerization enzyme used is Klenow fragment in a 10× reaction buffer (500 mM Tris-HCl (pH 8.0 at 25° C.), 50 mM $MgCl_2$, 10 mM DTT) from Fermentas, USA; Deoxynucleotide triphosphates (dNTP) from Qiagen, USA; Standard buffers.

DNA Hybridization onto the Micro-Beads:

Single stranded biotin-DNA in Tris Buffer (20 mM Tris-HCl buffer, 140 mM NaCl, 20 mM KCl, pH 7.5) was heated at 90° C. for 5 minutes and slowly cooled down to 25° C. at 0.1° C./min. The product was self-primed DNA.

250 μl of 1 mg/50 μl streptavidin-coated magnetic beads was washed with 1 mL of 20 mM Tris-Buffer and then dispersed in 250 μl of the same buffer. Next, 10 nmol of biotin-DNA was added to the solution, followed by incubation on a rotator at room temperature for 2 hours. The excess DNA not bound to the beads was washed away with 500 μl of Tris-buffer for five times. The highest capacity of the beads for biotin DNA is 0.3 nmol/1 mg. At last, the beads were dispersed in 250 μl of 1× Klenow reaction buffer to make a 1 mg/50 μl beads solution.

DNA Polymerization Protocol:

100 μL of magnetic beads (1 mg/50 μL) were deposited in the reservoir on top of the CMOS chip. 5 μL of Klenow enzyme (5 units/μL) was added. The Ag/AgCl reference electrode was dipped into the reservoir. The CMOS chip was subsequently activated and the real time data were captured on a PC when dNTPs were added one at a time.

Measuring Interface Capacitance vs. pH:

150 μL of Tris-HCl buffer (pH 8.0) was deposited in the reservoir on top of the CMOS chip. The reference electrode (Ag/AgCl) was dipped into the reservoir. Sinusoids of amplitude 10 mV and frequency ranging between 1-10 kHz were applied to the reference electrode. The pixel output amplitude was measured, which was then used to estimate the interface capacitance $C_1$. The pH was changed in steps by adding 1-5 μL quantities of 120 mM HCl The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

---

SEQUENCE LISTING

<160> NUMBER OF SEQ ID NOS: 1

<210> SEQ ID NO 1

<211> LENGTH: 55

<212> TYPE: DNA

<213> ORGANISM: Artificial Sequence

<220> FEATURE:

<223> OTHER INFORMATION: Primer

<400> SEQUENCE: 1
cctctgagtc aaaaaaaagc cgtcgttata caacggaacg ttgtataacg acggc    55

---

SEQUENCE LISTING

<160> NUMBER OF SEQ ID NOS: 1

<210> SEQ ID NO 1
<211> LENGTH: 55
<212> TYPE: DNA
<213> ORGANISM: Artificial Sequence
<220> FEATURE:
<223> OTHER INFORMATION: Primer

<400> SEQUENCE: 1
cctctgagtc aaaaaaaagc cgtcgttata caacggaacg ttgtataacg acggc    55

The invention claimed is:

1. A method for identifying the presence of a nucleic acid molecule in an individual well, comprising:
   (a) providing (i) a microwell structure comprising a plurality of wells, wherein an individual well of said plurality of wells comprises a porous polymer and said nucleic acid molecule immobilized to said porous polymer, and wherein said individual well is configured to contain a mixture comprising an electrically-conductive solution and reagents necessary for performing a polymerization reaction on said nucleic acid molecule, and (ii) a sensor adjacent to said individual well, wherein said sensor comprises an active electrode that is capacitively coupled to said mixture and is configured to detect an electrical signal from said individual well during said polymerization reaction;
   (b) subjecting said nucleic acid molecule to said polymerization reaction under conditions that are sufficient to generate a nucleic acid strand that is complementary to said nucleic acid molecule;
   (c) detecting said electrical signal from said individual well during said polymerization reaction using said sensor, wherein said electrical signal is a localized ionic current in said individual well based on an imbalance between absorbed free ionic charges and released free ionic charges in an electrolyte near said nucleic acid molecule of said individual well; and
   (d) identifying the presence of said nucleic acid molecule in said individual well based on said electrical signal detected in step (c).

2. The method of claim 1, wherein said sensor further comprises an insulating layer adjacent to said active electrode.

3. The method of claim 2, wherein said insulating layer has a thickness between about 5 nanometers (nm) and 100 nm.

4. The method of claim 1, wherein said sensor further comprises a detection circuitry operatively coupled to said active electrode.

5. The method of claim 4, wherein said detection circuitry comprises an operational amplifier and a capacitor that is in a parallel configuration with respect to said operational amplifier.

6. The method of claim 1, wherein said template nucleic acid molecule is self-primed.

7. The method of claim 1, wherein said nucleic acid molecule is immobilized on a surface of said porous polymer using linkers.

8. The method of claim 1, wherein said reagents necessary for performing said polymerization reaction include a polymerase and nucleotides.

9. The method of claim 1 further comprising:
   adding a plurality of nucleotides of a single type to said individual well to trigger said polymerization reaction;
   detecting said electrical signal after said adding a plurality of nucleotides of said single type; and
   removing the nucleotides of said single type unused in said polymerization reaction from said individual well.

10. The method of claim 9, further comprising introducing a plurality of nucleotides of another single type into said individual well and polymerizing said nucleic acid molecule using said plurality of nucleotides of said another single type.

11. The method of claim 1, wherein said electrical signal is detected within an interface double layer of said active electrode.

12. The method of claim 1, wherein said electrical signal is detected in real time while said polymerization reaction is performed.

13. The method of claim 1, wherein said plurality of wells comprises an additional well, wherein said additional well comprises an additional nucleic acid molecule.

14. The method of claim 1, wherein said nucleic acid molecule comprises a plurality of nucleic acid molecules, each of which is immobilized on a surface of said porous polymer.

15. The method of claim 14, wherein said plurality of nucleic acid molecules are identical.

* * * * *